(12) United States Patent
Sklaroff

(10) Patent No.: US 12,288,600 B2
(45) Date of Patent: Apr. 29, 2025

(54) GENERATIVE MACHINE LEARNING ON TEXTUAL QUERIES RELATING TO MOLECULES

(71) Applicant: Genesis Therapeutics, Inc., Burlingame, CA (US)

(72) Inventor: Ben Sklaroff, San Francisco, CA (US)

(73) Assignee: Genesis Therapeutics, Inc., Burlingame, CA (US)

( * ) Notice: Subject to any disclaimer, the term of this patent is extended or adjusted under 35 U.S.C. 154(b) by 0 days.

(21) Appl. No.: 18/408,042

(22) Filed: Jan. 9, 2024

(65) Prior Publication Data

US 2024/0233883 A1 Jul. 11, 2024

Related U.S. Application Data

(60) Provisional application No. 63/510,599, filed on Jun. 27, 2023, provisional application No. 63/460,421, (Continued)

(51) Int. Cl.
*G16C 20/70* (2019.01)
*G16C 20/40* (2019.01)
*G16C 20/90* (2019.01)

(52) U.S. Cl.
CPC ............ *G16C 20/70* (2019.02); *G16C 20/40* (2019.02); *G16C 20/90* (2019.02)

(58) Field of Classification Search
CPC .......... G03N 3/08; G16C 20/70; G16C 20/90; G16C 20/40
See application file for complete search history.

(56) References Cited

U.S. PATENT DOCUMENTS 11,080,607 B1 * 8/2021 Demtchenko .......... G06N 3/044
11,176,462 B1 * 11/2021 Bastas .................... G16B 50/10
(Continued)

FOREIGN PATENT DOCUMENTS

WO WO-2020244775 A1 * 12/2020 ......... G06F 16/3344
WO WO-2022059021 A1 * 3/2022 ............. G06N 20/00

OTHER PUBLICATIONS

Su, B., "A Molecular Multimodal Foundation Model Associating Molecule Graphs with Natural Language", *arXiv e-prints*, Art. No. arXiv:2209.05481, 2022. doi:10.48550/arXiv.2209.05481 (Year: 2022).*

(Continued)

*Primary Examiner* — Yoshihisa Ishizuka
(74) *Attorney, Agent, or Firm* — Fish & Richardson P.C.

(57) ABSTRACT

Methods, systems, and apparatus, including computer programs encoded on a computer storage medium, for generating a response to a textual query relating to one or more molecules. In one aspect, a method comprises: receiving, from a user, data defining: (i) a chemical structure of each of one or more input molecules, and (ii) a textual query related to the one or more input molecules; generating a sequence of input tokens that jointly represents: (i) the chemical structure of each input molecule, and (ii) the textual query; and processing the sequence of input tokens that jointly represents: (i) the chemical structure of each input molecule, and (ii) the textual query, using a generative neural network to generate a sequence of output tokens defining data responsive to the textual query.

20 Claims, 10 Drawing Sheets

Related U.S. Application Data filed on Apr. 19, 2023, provisional application No. 63/437,832, filed on Jan. 9, 2023.

(56) References Cited

U.S. PATENT DOCUMENTS

| | | | | |
|---|---|---|---|---|
| 2008/0040342 | A1* | 2/2008 | Hust | G06F 16/355 |
| | | | | 707/999.005 |
| 2019/0286791 | A1* | 9/2019 | Takeda | G16C 20/30 |
| 2019/0340236 | A1* | 11/2019 | Le | G06F 40/30 |
| 2020/0026765 | A1* | 1/2020 | Jaitly | G10L 15/197 |
| 2022/0101972 | A1* | 3/2022 | Bajpai | G16H 70/40 |
| 2022/0253477 | A1* | 8/2022 | Lipka | G06N 20/00 |

OTHER PUBLICATIONS

Flam-Shepherd et al., "Language models can learn complex molecular distributions," Nature Communications, Jun. 7, 2022, 13(3293):1-10.
International Search Report and Written Opinion in International Appln. No. PCT/US2024/010849, mailed on Jun. 6, 2024, 13 pages.
Taylor et al., "Galactica: A Large Language Model for Science," arXiv preprint, arXiv:2211.09085, Nov. 26, 2022, 58 pages.

* cited by examiner

GENERATIVE MACHINE LEARNING ON TEXTUAL QUERIES RELATING TO MOLECULES

CROSS-REFERENCE TO RELATED APPLICATIONS

This application claims the benefit of priority to U.S. Application No. 63/437,832, filed on Jan. 9, 2023, U.S. Application No. 63/460,421, filed on Apr. 19, 2023, and U.S. Application No. 63/510,599, filed on Jun. 27, 2023, the contents of which are hereby incorporated by reference.

BACKGROUND

This specification relates to a computational platform for generating molecules.

Drugs can be molecules that elicit a therapeutic response by binding to a target biological molecule. Once bound, the ligand can either inhibit the binding of other ligands or allosterically adjust the target's conformation. Binding is thus crucial to the behavior of therapeutic ligands. Maximizing a molecule's therapeutic effect can involve maximizing the affinity of the molecule for desired targets while minimizing the affinity of the molecule for off-target binding sites.

Machine learning models can be used to generate predictions. Machine learning models receive an input and generate an output, e.g., a predicted output, based on the received input. Some machine learning models are parametric models and generate the output based on the received input and on values of the parameters of the model. Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification generally describes a system implemented as computer programs on one or more computers in one or more locations that implements a computational platform for generating data representing molecules.

Throughout this specification, a "machine learning model" can be any appropriate type of machine learning model, e.g., a model that includes one or more of: a neural network model, or a support vector machine model, or a random forest model, or a decision tree model, or a linear regression model, and so forth.

Throughout this specification, any described machine learning model can have any appropriate machine learning model architecture that enables the machine learning model to perform its described functions. For instance, any described neural network can have a neural network architecture that includes any appropriate types of neural network layers (e.g., fully connected layers, attention layers, recurrent layers, convolutional layers, message passing layers, and so forth) in any appropriate number (e.g., 5 layers, or 10 layers, or 100 layers) and connected in any appropriate configuration (e.g., as a directed graph of layers).

Throughout this specification, the term "token" can refer to data representing a discrete element. For instance, a token can represent a feature of a molecule, e.g., an atom, bond, branch, ring structure, atomic charge, and so forth, in a molecule. As another example, a token can represent a part of a chemical computation operation, e.g., by at least partially defining or parametrizing a molecule generation operation, or molecule filtering operation, or a chemical computation graph (as will be described in more detail below).

Sequences of tokens can represent larger entities, such as a molecules or groups of molecules, or entire chemical computation operations. For instance, a molecule can be represented as a sequence of tokens expressed in a Simplified Molecular Input Line Entry System (SMILES) format or International Chemical Identifier (InChI) format. As another example, a set of molecules and a chemical computation operation to be applied to the set of molecules can be expressed by a sequence of tokens that includes tokens representing the molecules and tokens defining the parameters of the chemical computation operation.

According to one aspect, there is provided a method performed by one or more computers, the method comprising: receiving, from a user, a request to generate data identifying candidate molecules satisfying one or more molecular criteria; generating a collection of candidate molecules that satisfy the one or more molecular criteria; generating, for each candidate molecule in the collection of candidate molecules, one or more molecular scores that characterize one or more properties of the candidate molecule; filtering the collection of candidate molecules, based on the molecular scores, to remove a plurality of candidate molecules from the collection of candidate molecules; and after filtering the collection of candidate molecules based on the molecular scores, providing a representation of the collection of candidate molecules to the user.

In some implementations, receiving, from the user, the request to generate data identifying molecules satisfying one or more molecular criteria comprises: receiving, from the user, data identifying: (i) a first set of one or more molecules, and (ii) a second set of one or more molecules; wherein a candidate molecule is designated as satisfying the molecular criteria if the candidate molecule results from attaching a first molecule from the first set of molecules and a second molecule from the second set of molecules.

In some implementations, the method further comprises: receiving, from the user, data designating one or more attachment points on each molecule in the first set of molecules; wherein a candidate molecule is designated as satisfying the molecular criteria if the candidate molecule results from attaching a first molecule from the first set of molecules and a second molecule from the second set of molecules at an attachment point of the first molecule.

In some implementations, the method further comprises: receiving, from the user, data designating one or more attachment points on each molecule in the second set of molecules; wherein a candidate molecule is designated as satisfying the molecular criteria if the candidate molecule results from attaching a first molecule from the first set of molecules and a second molecule from the second set of molecules at the respective attachment points of the first molecule and the second molecule.

In some implementations, receiving, from the user, the request to generate data identifying molecules satisfying one or more molecular criteria comprises: receiving, from the user, data identifying: (i) a molecule, wherein one or more portions of the molecule are designated for replacement, and (ii) a set of one or more molecular fragments; wherein a candidate molecule is designated as satisfying the molecular criteria if the candidate molecule results from replacing each portion of the molecule that is designated for replacement by a respective molecular fragment from the set of molecular fragments.

In some implementations, the method further comprises: receiving, from the user, data designating one or more attachment points on the molecule; wherein replacing a portion of the molecule that is designated for replacement by a respective molecular fragment from the set of molecular fragments comprises: attaching the molecular fragment to the molecule at an attachment point on the molecule.

In some implementations, receiving, from the user, the request to generate data identifying molecules satisfying one or more molecular criteria comprises: receiving, from the user, data identifying a first set of one or more molecules; wherein a candidate molecule is designated as satisfying the molecular criteria if the candidate molecule is predicted to result from a chemical reaction involving a first molecule from the first set of molecules.

In some implementations, receiving, from the user, the request to generate data identifying molecules satisfying one or more molecular criteria further comprises: receiving, from the user, data identifying a second set of one or more molecules; wherein a candidate molecule is designated as satisfying the molecular criteria if the candidate molecule is predicted to result from a chemical reaction involving a first molecule from the first set of molecules and a second molecule from the second set of molecules.

In some implementations, receiving, from the user, the request to generate data identifying molecules satisfying one or more molecular criteria further comprises: receiving, from the user, a selection of one or more chemical reactions; wherein a candidate molecule is designated as satisfying the molecular criteria if the candidate molecule is predicted to result from chemically reacting a first molecule from the first set of molecules and a second molecule from the second set of molecules in accordance with the selected chemical reactions.

In some implementations, receiving, from the user, the request to generate data identifying molecules satisfying one or more molecular criteria further comprises: receiving, from the user, data designating: (i) a respective reactive portion of each molecule in the first set of molecules, and (ii) a respective reactive portion of each molecule in the second set of molecules; wherein a candidate molecule is designated as satisfying the molecular criteria if the candidate molecule is predicted to result from chemically reacting the reactive portion of a first molecule in the first set of molecules with the reactive portion of a second molecule in the second set of molecules.

In some implementations, for each of one or more molecules in the first set of molecules or the second set of molecules, a proper subset of a set of atoms included in the molecule is designated as being a reactive portion of the molecule.

In some implementations, for each of one or more molecules in the first set of molecules or the second set of molecules, every part of the molecule is designated as being a reactive portion of the molecule.

In some implementations, generating the collection of candidate molecules that satisfy the one or more molecular criteria comprises determining, for each first molecule in the first set of molecules and each second molecule in the second set of molecules, a result of chemically reacting the first molecule with the second molecule.

In some implementations, determining a result of chemically reacting a first molecule with a second molecule comprises generating one or more candidate molecules that result from chemically reacting the first molecule with the second molecule.

In some implementations, generating the one or more candidate molecules that result from chemically reacting the first molecule with the second molecule comprises performing a computational simulation of a chemical reaction between the first molecule and the second molecule.

In some implementations, generating the one or more candidate molecules that result from chemically reacting the first molecule with the second molecule comprises processing a network input derived from the first molecule and the second molecule using a reactivity neural network to generate a network output that defines a predicted reactivity of the first molecule with the second molecule.

In some implementations, the reactivity neural network comprises one or more graph neural network layers, or one or more attention neural network layers, or both.

In some implementations, determining a result of chemically reacting a first molecule with a second molecule comprises: determining that the first molecule does not chemically react with the second molecule.

In some implementations, receiving, from the user, the request to generate data identifying molecules satisfying one or more molecular criteria comprises: receiving a representation of a scaffold molecule as a sequence of tokens, wherein one or more of the tokens are masked tokens; wherein a candidate molecule is designated as satisfying the molecular criteria if the candidate molecule can be represented by a sequence of tokens generated by replacing each masked token in the sequence of tokens representing the scaffold molecule by one or more non-masked tokens.

In some implementations, receiving the representation of the scaffold molecule as the sequence of tokens comprises: providing, to a user, a representation of a scaffold molecule; receiving, from the user, a user input that selects one or more atoms in the scaffold molecule to be masked; and determining the representation of the scaffold molecule as the sequence of tokens, comprising masking each token that corresponds to an atom that the user has selected to be masked.

In some implementations, the method further comprises: receiving, from the user, data specifying one or more target molecular fragments, wherein each target molecular fragment corresponds to a respective masked token; wherein replacing each masked token in the sequence of tokens representing the scaffold molecule by one or more non-masked tokens comprises, for one or more masked tokens: replacing the masked token by one or more non-masked tokens that define a molecular fragment that is an isostere of a target molecular fragment for the masked token.

In some implementations, the method further comprises: receiving, from the user, data specifying a protein binding site corresponding to a given masked token; wherein replacing each masked token in the sequence of tokens representing the scaffold molecule by one or more non-masked tokens comprises, for the given masked token: replacing the given masked token by one or more non-masked tokens that define a molecular fragment that has a conformation that is complementary to the conformation of the protein binding site.

In some implementations, generating the collection of candidate molecules that satisfy the one or more molecular criteria comprises, for each candidate molecule, sequentially unmasking each masked token in the sequence of tokens representing the scaffold molecule starting from a first masked token, comprising, for each masked token: processing a network input that comprises each token preceding the masked token in the sequence of tokens representing the scaffold molecule, using a molecular generation neural network, to generate a score distribution over a set of non-masked tokens; selecting a non-masked token from the set of non-masked tokens in accordance with the score distribution; and replacing the masked token by a sequence of one or more non-masked tokens that includes the selected non-masked token.

In some implementations, for each masked token, selecting a token from the set of non-masked tokens in accordance with the score distribution comprises randomly sampling a non-masked token from the set of non-masked tokens in accordance with the score distribution over the set of non-masked tokens.

In some implementations, the molecular generation neural network has been trained on a set of training examples to perform an unmasking task, wherein: each training example comprises: (i) a partially-masked representation of a training molecule as a sequence of tokens, wherein each one or more of the tokens are masked tokens, and (ii) a non-masked representation of the training molecule as the sequence of tokens, wherein each token is a non-masked token; and training the molecular generation neural network on a training example comprises training the molecular generation neural network to process the partially-masked representation of the training molecule to generate the non-masked representation of the training molecule.

In some implementations, the molecular generation neural network comprises one or more attention neural network layers.

In some implementations, the molecular generation neural network comprises one or more recurrent neural network layers.

In some implementations, generating the collection of candidate molecules that satisfy the one or more molecular criteria comprises generating each candidate molecule by replacing the masked tokens in the sequence of tokens representing the scaffold molecule by non-masked tokens representing a respective molecular fragment, wherein each molecular fragment is selected from a set of molecular fragments.

In some implementations, the set of molecular fragments is generated at least in part by fragmenting each molecule in a library of molecules.

In some implementations, the set of molecular fragments is generated at least in part by a generative neural network.

In some implementations, the set of molecular fragments is generated at least in part by systematically enumerating every molecular fragment satisfying a set of generation criteria.

In some implementations, for each candidate molecule in a collection of candidate molecules, one or more molecular scores for the candidate molecule characterizes one or more of: a binding affinity of the candidate molecule for a binding target; a solubility of the candidate molecule; a toxicity of the candidate molecule; a binding affinity of the candidate molecule for one or more off-target binding sites; an absorption property of the candidate molecule; a distribution property of the candidate molecule; a metabolism property of the candidate molecule; an excretion property of the candidate molecule; a molecular weight property of the candidate molecule; or a topological polar surface area of the candidate molecule.

In some implementations, filtering the collection of candidate molecules further comprises, for each candidate molecule: determining whether the candidate molecule satisfies a matching criterion with each filtering molecule in a set of filtering molecules; and determining whether to filter the candidate molecule based at least in part on whether the candidate molecule satisfies the matching criterion with each filtering molecule in the set of filtering molecules.

In some implementations, for each of one or more candidate molecules, determining whether to filter the candidate molecule comprises: determining that the candidate molecule satisfies the matching criterion with at least one filtering molecule in the set of filtering molecules; and in response, filtering the candidate molecule.

In some implementations, for each of one or more candidate molecules, determining whether to filter the candidate molecule comprises: determining that the candidate molecule does not satisfy the matching criterion with any of the filtering molecules in the set of filtering molecules; and in response, filtering the candidate molecule.

In some implementations, for each candidate molecule in the collection of candidate molecules, generating the one or more molecular scores for the candidate molecule comprises processing a representation of the candidate molecule using a scoring machine learning model, in accordance with values of a set of scoring machine learning model parameters, to generate a molecular score for the candidate molecule.

In some implementations, the scoring machine learning model comprises a neural network model.

In some implementations, for each candidate molecule in the collection of candidate molecules, generating the one or more molecular scores for the candidate molecule comprises: generating a molecular score for the candidate molecular based on a physics-based simulation of the candidate molecule.

In some implementations, the method further comprises, after filtering the collection of candidate molecules, rescoring each candidate molecule in the collection of candidate molecules, comprising, for each candidate molecule in the collection of candidate molecules: processing a representation of the candidate molecule using a high-fidelity scoring model to generate one or more high-fidelity molecular scores for the candidate molecule.

In some implementations, the high-fidelity scoring model is predicted to be more accurate than the scoring machine learning model.

In some implementations, the high-fidelity scoring model has a greater number of model parameters than the scoring machine learning model.

In some implementations, the high-fidelity scoring model performs a greater number of operations than the scoring machine learning model to generate a score for a candidate molecule.

In some implementations, the high-fidelity scoring model comprises a machine learning model, or a physics-based model, or a combination of a machine learning model and a physics-based model.

In some implementations, the method further comprises: generating a set of training examples for training the scoring machine learning model, wherein each training example corresponds to a candidate molecule and comprises: (i) a representation of the candidate molecule, and (ii) a high-fidelity molecular score generated by the high-fidelity scoring model for the candidate molecule; and training the scoring the machine learning model on the set of training examples.

In some implementations, training the scoring machine learning model on the set of training examples comprises, for each training example: training the scoring machine learning model to process the representation of the candidate molecule of the training example to generate a molecular score for the candidate molecules that matches the high-fidelity molecular score of the training example.

In some implementations, filtering the collection of candidate molecules comprises, for each of a plurality of candidate molecules: determining that a molecular score for the candidate molecule fails to satisfy a threshold; and in response, removing the candidate molecule from the collection of candidate molecules.

In some implementations, providing a representation of the collection of candidate molecules to the user comprises presenting the collection of candidate molecules on a user interface of a user device of the user, comprising displaying visual representations of some or all of the candidate molecules in the collection of candidate molecules by way of the user interface.

In some implementations, providing a representation of the collection of candidate molecules to the user comprises storing the representation of the collection of candidate molecules in a memory.

In some implementations, providing the representation of the collection of candidate molecules to the user comprises determining a ranking of the collection of candidate molecules based on the molecular scores.

In some implementations, providing the representation of the collection of candidate molecules to the user comprises: providing, to the user, an interface that enables the user to specify one or more sorting or filtering criteria for the collection of candidate molecules based on the molecular scores for the candidate molecules.

In some implementations, the method further comprises: selecting one or more candidate molecules from the collection of candidate molecules for physical synthesis.

In some implementations, the method further comprises: physically synthesizing the selected candidate molecules.

In some implementations, the method further comprises, for each of the physically synthesized candidate molecules: experimentally testing one or more properties of the physically synthesized candidate molecule.

In some implementations, the method further comprises: selecting one or more of the candidate molecules for inclusion in a drug; and determining that the drug should be administered to a subject.

In some implementations, the method further comprises: selecting one or more of the candidate molecules for inclusion in a drug to be administered to one or more subjects.

In some implementations, generating the collection of candidate molecules that satisfy the one or more molecular criteria comprises: generating at least 1000 candidate molecules.

In some implementations, the at least 1000 candidate molecules are generated in under 1 second.

In some implementations, receiving, from the user, the request to generate data identifying molecules satisfying one or more molecular criteria comprises receiving the user input from the user by way of a graphical user interface.

In some implementations, the graphical user interface comprises interactive elements that enable the user to input one or more of: one or more sets of input molecules; a chemical computation graph, including designating one or more chemical computation nodes of the chemical computation graph as output nodes; one or more filtering criteria for filtering sets of candidate molecules; or one or more scaffold molecules and operations for replacing masked tokens in the scaffold molecules.

According to another aspect, there is provided a method performed by one or more computers, the method comprising: receiving, from a user, data defining a chemical computation graph, wherein: the chemical computation graph comprises a set of chemical computation nodes and a set of edges; each chemical computation node is configured to perform operations comprising: receiving a set of input molecules; and processing the set of input molecules, in accordance with a sequence of one or more transformation operations associated with the chemical computation node, to generate a set of output molecules; and each edge connects a respective first chemical computation node to a respective second chemical computation node and defines that a respective set of output molecules generated by the first chemical computation node should be provided as a respective set of input molecules to a second chemical computation node; and generating a set of candidate molecules using the chemical computation graph.

In some implementations, receiving data defining the chemical computation graph further comprises: receiving data designating one or more chemical computation nodes in the chemical computation graph as input nodes, wherein each input node is configured to receive a set of input molecules specified by the user.

In some implementations, receiving data defining the chemical computation graph further comprises: receiving data designating one or more chemical computation nodes in the chemical computation graph as being output nodes, wherein the output molecules generated by the outputs nodes collectively define the set of candidate molecules generated using the chemical computation graph.

In some implementations, generating the set of candidate molecules using the chemical computation graph comprises: providing a respective set of input molecules to each chemical computation node in the chemical computation graph that is designated as an input node; and executing the chemical computation graph to generate, from each chemical computation node that is designated as an output node, a respective set of output molecules.

In some implementations, executing the chemical computation graph comprises executing a plurality of chemical computation nodes in the chemical computation graph in parallel by a plurality of computing units.

In some implementations, for each of one or more chemical computation nodes in the chemical computation graph, the sequence of one or more transformation operations comprises one or more molecule generation operations, wherein each molecule generation operation is parameterized by a set of molecular generation criteria and operates on a set of input molecules to generate a set of output molecules, wherein each output molecule satisfies the set of molecular generation criteria.

In some implementations, for one or more of the molecule generation operations, the set of molecular generation criteria comprise an attachment criteria specifying that: (i) each output molecule should be generated by attaching two or more input molecules, or (ii) each output molecule should be generated by replacing one or more portions of an input molecule with a respective molecular fragment from a set of molecular fragments.

In some implementations, for one or more of the molecule generation operations, the set of molecular generation criteria comprise chemical reaction criteria specifying that output molecules are generated by chemically reacting one or more input molecules in accordance with one or more chemical reactions.

In some implementations, for one or more of the molecule generation operations, the set of molecular generation criteria comprise scaffolding criteria specifying that output molecules are generated as completions of scaffold molecules, wherein each scaffold molecule is an input molecule where one or more tokens in a sequence of tokens representing the input molecule are masked.

In some implementations, for each of one or more chemical computation nodes in the chemical computation graph, the sequence of one or more transformation operations comprises one or more molecule filtering operations, wherein each molecule filtering operation is parametrized by a set of filtering criteria and operates on a set of input molecules to remove any molecules from the set of input molecules that satisfy one or more filtering criteria in the set of filtering criteria.

In some implementations, for one or more of the molecule filtering operations, the set of filtering criteria are based on molecular scores of input molecules, wherein a molecular score for an input molecule characterizes a property of the input molecule.

In some implementations, for each of one or more chemical computation nodes in the chemical computation graph, the sequence of one or more transformation operations comprises a chemical reaction operation, wherein applying the chemical reaction operation to a set of initial molecules comprises: processing the set of initial molecules to generate a set final molecules, wherein each final molecule is predicted to result from a chemical reaction involving a pair of initial molecules from the set of initial molecules.

In some implementations, for each of one or more chemical computation nodes in the chemical computation graph, the sequence of one or more transformation operations comprises a molecule filtering operation, wherein applying the filtering operation to a set of initial molecules comprises: processing the set of initial molecules to generate, for each initial molecule in the set of initial molecules, one or more molecular scores that characterize one or more properties of the set of initial molecules; and filtering the set of initial molecules, based on the molecular scores, to generate a final set of molecules, wherein filtering the set of initial molecules comprises removing one or more molecules from the set of initial molecules.

In some implementations, for each of one or more chemical computation nodes in the chemical computation graph, processing the set of input molecules to generate a set of output molecules comprises: applying a chemical reaction operation to the set of input molecules to generate a set of intermediate molecules, wherein each intermediate molecule is predicted to result from a chemical reaction involving a pair of input molecules from the set of input molecules; and applying a filtering operation to the set of intermediate molecules, comprising: generating, for each intermediate molecule in the set of intermediate molecules, one or more molecular scores that characterize one or more properties of the set of intermediate molecules; and filtering the set of intermediate molecules, based on the molecular scores, to generate the set of output molecules, wherein filtering the set of intermediate molecules comprises removing one or more molecules from the set of intermediate molecules.

In some implementations, the chemical computation graph comprises a cyclical sub-graph, and wherein executing the chemical computation graph comprises iteratively executing the cyclical sub-graph over a sequence of iterations until a termination criterion from a set of termination criteria is satisfied.

In some implementations, the set of termination criteria includes a termination criterion that is satisfied when the cyclical sub-graph has been executed over a predefined number of iterations.

In some implementations, the set of termination criteria includes a termination criterion that is evaluated based on molecular scores associated with molecules generated by one or more chemical computation nodes in the cyclical sub-graph.

In some implementations, the chemical computation graph comprises a non-linear configuration of nodes.

In some implementations, the chemical computation graph includes edges that connect one chemical computation node to two or more other chemical computation nodes.

In some implementations, the chemical computation graph includes edges that connect two or more chemical computation nodes to one other chemical computation node.

In some implementations, the chemical computation graph includes at least five chemical computation nodes.

In some implementations, the method further comprises selecting one or more candidate molecules from the set of candidate molecules for physical synthesis.

In some implementations, the method further comprises physically synthesizing the selected candidate molecules.

In some implementations, the method further comprises, for each of the physically synthesized candidate molecules: experimentally testing one or more properties of the physically synthesized candidate molecule.

In some implementations, the method further comprises: selecting one or more of the candidate molecules for inclusion in a drug; and determining that the drug should be administered to a subject.

In some implementations, the method further comprises: selecting one or more of the candidate molecules for inclusion in a drug to be administered to one or more subjects.

According to another aspect, there is provided a method performed by one or more computers, the method comprising: receiving, from a user, data defining: (i) a chemical structure of each of one or more input molecules, and (ii) a textual query related to the one or more input molecules; generating a sequence of input tokens that jointly represents: (i) the chemical structure of each input molecule, and (ii) the textual query; and processing the sequence of input tokens that jointly represents: (i) the chemical structure of each input molecule, and (ii) the textual query, using a generative neural network to generate a sequence of output tokens defining data responsive to the textual query.

In some implementations, the generative neural network is an autoregressive neural network.

In some implementations, generating the sequence of output tokens defining data responsive to the textual query comprises sequentially generating each output token in the sequence of output tokens starting from a first output token in the sequence of output tokens.

In some implementations, for one or more positions in the sequence of output tokens, generating the output token at the position comprises: processing a network input that comprises a respective output token at each of one or more preceding positions in the sequence of output tokens, using the generative neural network, to generate a score distribution over a set of possible tokens; and selecting the output token for the position in accordance with the score distribution.

In some implementations, for one or more positions in the sequence of output tokens, the network input to the generative neural network further comprises the sequence of input tokens.

In some implementations, for one or more positions in the sequence of output tokens, the network input to the generative neural network further comprises a predefined sequence of context tokens representing at least chemical structure data.

In some implementations, for one or more positions in the sequence of output tokens, selecting the output token for the position in accordance with the score distribution comprises: randomly sampling a token from the set of possible tokens in accordance with the score distribution over the set of possible tokens.

In some implementations, the method further comprises, for one or more positions in the sequence of output tokens, after selecting the output token for the position: determining that a suffix of the sequence of output tokens defines a chemical computation operation; in response, executing the chemical computation operation to generate data defining a set of molecules; and appending tokens representing the set of molecules generated by the chemical computation operation to the sequence of output tokens.

In some implementations, executing the chemical computation operation comprises performing a molecule generation operation, wherein the molecule generation operation is parameterized by a set of molecular generation criteria and operates on a set of input molecules to generate a set of output molecules, wherein each output molecule satisfies the set of molecular generation criteria.

In some implementations, the set of molecular generation criteria comprise an attachment criteria specifying that: (i) each output molecule should be generated by attaching two or more input molecules, or (ii) each output molecule should be generated by replacing one or more portions of an input molecule with a respective molecular fragment from a set of molecular fragments.

In some implementations, the set of molecular generation criteria comprise chemical reaction criteria specifying that output molecules are generated by chemically reacting one or more input molecules in accordance with one or more chemical reactions.

In some implementations, the set of molecular generation criteria comprise scaffolding criteria specifying that output molecules are generated as completions of scaffold molecules, wherein each scaffold molecule is an input molecule where one or more tokens in a sequence of tokens representing the input molecule are masked.

In some implementations, executing chemical computation operation comprises performing a molecule filtering operation, wherein the molecule filtering operation is parametrized by a set of filtering criteria and operates on a set of input molecules to remove any molecules from the set of input molecules that satisfy one or more filtering criteria in the set of filtering criteria.

In some implementations, the set of filtering criteria are based on molecular scores of input molecules, wherein a molecular score for an input molecule characterizes a property of the input molecule.

In some implementations, executing the chemical computation operation comprises executing a chemical computation graph.

In some implementations, the generative neural network comprises one or more attention neural network layers.

In some implementations, processing the sequence of input tokens that jointly represents: (i) the chemical structure of each input molecule, and (ii) the textual query, using the generative neural network comprises: processing the sequence of input tokens in accordance with trained values of a set of generative neural network parameters; wherein the generative neural network parameters have been trained, by a machine learning training technique, on a set of training examples.

In some implementations, the generative neural network has been trained by operations comprising: pre-training the generative neural network on a first set of training examples, wherein one or more of the training examples in the first set of training examples each comprise a respective sequence of tokens representing natural language text; and fine-tuning the generative neural network on a second set of training examples, wherein one or more of the training examples in the second set of training examples each comprise a respective sequence of tokens representing natural language text and chemical structure data.

In some implementations, the generative neural network has been trained by operations comprising: training the generative neural network on a set of training examples that comprises: (i) a plurality of training examples that each comprise a respective sequence of tokens representing natural language text, and (ii) a plurality of training examples that each comprise a respective sequence of tokens representing natural language text and chemical structure data.

In some implementations, the method further comprises: determining gradients of an objection function that measures an error in the sequence of output tokens generated by the generative neural network; and updating current values of a set of generative neural network parameters of the generative neural network using the gradients.

In some implementations, updating the current values of the set of generative neural network parameters of the generative neural network using the gradients comprises: backpropagating the gradients through the generative neural network.

In some implementations, the sequence of output tokens defines a chemical structure of each of one or more output molecules, wherein the one or more output molecules are responsive to the textual query.

In some implementations, the sequence of output tokens defines a chemical computation graph, wherein executing the chemical computation graph causes generation of one or more output molecules that are responsive to the textual query.

In some implementations, the chemical computation graph comprises a set of chemical computation nodes and a set of edges; each chemical computation node is configured to perform operations comprising: receiving a first set of molecules; and processing the first set of molecules, in accordance with a sequence of one or more transformation operations associated with the chemical computation node, to generate a second set of molecules; and each edge connects a respective first chemical computation node to a respective second chemical computation node and defines that a set of molecules generated by the first chemical computation node should be provided as an input to a second chemical computation node.

In some implementations, the method further comprises executing the chemical computation graph to generate one or more output molecules that are responsive to the textual query.

In some implementations, the method further comprises, at each of one or more iterations: executing at least a portion of a chemical computation graph generated by the generative neural network at a preceding iteration to generate one or more output molecules; and processing a sequence of tokens that jointly represents: (i) the one or more output molecules generated at the iteration, (ii) the chemical structure of each input molecule, and (iii) the textural query, using the generative neural network to generate a new chemical computation graph.

In some implementations, generating the sequence of input tokens that jointly represents: (i) the chemical structure of each input molecule, and (ii) the textual query, comprises: concatenating: (i) a sequence of tokens representing the chemical structure of each input molecule, and (ii) a sequence of tokens representing the textual query.

In some implementations, the sequence of tokens representing the chemical structure of each input molecule comprises one or more Simplified Molecular Input Line Entry System (SMILES) strings.

In some implementations, the textual query comprises a request to generate output molecules, based on the one or more input molecules, that satisfy one or more molecular criteria.

In some implementations, an output molecule is designated as satisfying a molecular criterion if the output molecule results from attaching a pair of input molecules.

In some implementations, the textual query designates one or more attachment points on each input molecule; and an output molecule is designated as satisfying a molecular criterion if the output molecule results from attaching a first input molecule and a second input molecule at the respective attachment points of the first input molecule and the second input molecule.

In some implementations, the textual query identifies: (i) one or more portions of each input molecule that are designated for replacement, and (ii) a set of one or more molecular fragments; and an output molecule is designated as satisfying a molecular criterion if the output molecule results from replacing each portion of an input molecule that is designated for replacement by a respective molecular fragment from the set of molecular fragments.

In some implementations, an output molecule is designated as satisfying a molecular criterion if the output molecule is predicted to result from a chemical reaction involving an input molecule.

In some implementations, an output molecule is designated as satisfying a molecular criterion if the output molecule is an isostere of an input molecule.

In some implementations, an output molecule is designated as satisfying a molecular criterion if a similarity measure between the output molecule and an input molecule satisfies a threshold.

In some implementations, an output molecule is designated as satisfying a molecular criterion if a molecular score of the output molecule is within target range.

In some implementations, the molecular score of the output molecule characterizes one or more of: a binding affinity of the output molecule for a binding target; a solubility of the output molecule; a toxicity of the output molecule; a binding affinity of the output molecule for one or more off-target binding sites; an absorption property of the output molecule; a distribution property of the output molecule; a metabolism property of the output molecule; an excretion property of the output molecule; a molecular weight property of the output molecule; or a topological polar surface area of the output molecule.

In some implementations, the method further comprise: selecting one or more of the output molecules for physical synthesis.

In some implementations, the method further comprises physically synthesizing the selected output molecules.

In some implementations, the method further comprises, for each of the physically synthesized output molecules: experimentally testing one or more properties of the physically synthesized output molecule.

In some implementations, the method further comprises: selecting one or more of the output molecules for inclusion in a drug; and determining that the drug should be administered to a subject.

In some implementations, the method further comprises selecting one or more of the output molecules for inclusion in a drug to be administered to one or more subjects.

According to another aspect, there is provided a system comprising: one or more computers; and one or more storage devices communicatively coupled to the one or more computers, wherein the one or more storage devices store instructions that, when executed by the one or more computers, cause the one or more computers to perform operations of the methods described herein.

According to another aspect, there are provided one or more non-transitory computer storage media storing instructions that when executed by one or more computers cause the one or more computers to perform operations of the method described herein.

Particular embodiments of the subject matter described in this specification can be implemented so as to realize one or more of the following advantages.

The system described in this specification provides a platform that can enable a user to leverage computational techniques to generate and screen large sets of molecules in order to identify molecules having certain characteristics, e.g., binding affinity, solubility, toxicity, etc. Molecules generated by the system can be candidate drug molecules, e.g., such that the system can be used to significantly accelerate the discovery of new drugs.

The system can include an interface that enables a user to precisely specify a set of molecules to be screened. For instance, the interface can enable a user to provide a set of input molecules, and to define the set of molecules to be screened as molecules resulting from combining, e.g., attaching or chemically reacting, pairs of molecules from the set of input molecules. The system can then implement computational techniques, e.g., machine learning models that predict chemical reactivity and molecular simulations to predict the results of chemical reactions, in order to computationally generate the set of molecules to be screened. As another example, the interface can enable a user to specify the set of molecules to be screened by providing a "scaffold" molecule, where certain parts of the scaffold molecules have been masked (e.g., left undefined). The system can process the scaffold molecule using a neural network to algorithmically generate a set of molecules that each represent a respective realization of the scaffold molecule, e.g., where the masked parts of the scaffold molecule have been replaced by concrete molecular structures. The system can train the neural network on large libraries of molecules, using machine learning training techniques, to generate realistic (e.g., stable) realizations of scaffold molecules. Through various implementations the system can thus use computational techniques, e.g., based on simulations and machine learning, to generate large sets of molecules that go well beyond what could be analyzed by a human or solely in the human mind.

The system can screen a set of molecules by generating one or more molecular scores for each molecule, and then filtering the set of molecules based on the molecular scores, e.g., to remove molecules having molecular scores that do not satisfy certain thresholds. The system can generate molecular scores for a molecule that characterize any appropriate property of the molecule, e.g., binding affinity, solubility, toxicity, etc., using computational techniques based on simulations and machine learning. Filtering the set of molecules can reduce the number of molecules, e.g., by one or more orders of magnitude, which can reduce consumption of resources. For instance, filtering the set of molecules can reduce consumption of computational resources, e.g., by reducing the amount of memory required to store the set of molecules, and by reducing computing power necessary to perform further processing of the set of molecules. As another example, filtering the set of molecules can reduce consumption of physical resources, e.g., laboratory resources, by reducing the number of molecules that are candidates for physical synthesis and testing.

The system can enable a user to define a chemical computation graph that includes a set of nodes (referred to as chemical computation nodes) and a set of edges. Each chemical computation node can be configured to process a set of input molecules, e.g., received from a user or from another chemical computation node, using a sequence of transformation operations (e.g., chemical reaction operations, filtering operations, or both), to generate a set of output molecules. Each edge connects a first chemical computation node to a second chemical computation node and defines that a set of molecules generated as an output of the first chemical computation node should be provided as an input to the second chemical computation node. The system can then execute the chemical computation graph to generate a set of candidate molecules, e.g., that have desired characteristics. The system can thus enable a user to generate candidate molecules by defining complex graphs of chemical reaction and filtering operations, which can vastly accelerate the process of discovering new drugs, e.g., by replacing weeks or months of physical experiments by second or minutes of computation.

The system described in this specification provides a user with the capability to precisely define and screen cross-sections of the space of possible molecules using computational methods. The system provides new capabilities both in terms of how cross-sections of the space of possible molecules can be defined (e.g., by configuring the topology of a chemical computation graph), and in terms of how candidate molecules are screened (e.g., by configuring the operations performed by the chemical computation nodes in the chemical computation graph). The operations performed by the system go well beyond what could be accomplished in the human mind or solely by a human, e.g., by enabling algorithmic generation of large sets of millions of molecules, and by enabling automated screening on molecules (e.g., using machine learning and computational simulation) to identify molecules having desired properties.

The system described in this specification can generate data responsive to free form textual queries relating to one or more input molecules. More specifically, the system can enable a user to submit data defining: (i) a respective chemical structure of each of one or more input molecules, and (ii) a free form textual query relating to the one or more input molecules. The system can generate a response to the textual query by serializing the input data into a sequence of tokens and processing the sequence of tokens using a generative neural network. The generative neural network be, e.g., an autoregressive neural network that iteratively and sequentially generates a sequence of output tokens that defines data, e.g., textual data or chemical structure data, that is responsive to the original textual query. The system thus provides a flexible interface that enables users to obtain responses to "open-vocabulary" queries, e.g., that are not constrained by a restrictive user interface that requires users to define queries by selecting from limited numbers of options available in predefined menus. The system can thus provide an improved interface for enabling users to obtain responses to queries relating to molecules, e.g., by broadening the range of possible queries that users can submit (e.g., to include any query expressible in free form text) and by reducing the technical expertise required of a user to interact with the system (e.g., because the user is merely required to express their query in text as opposed to, e.g., learning to navigate a complex user interface listing menus of predefined options).

As part of iteratively extending a sequence of output tokens responsive to a user query, the generative neural network can generate tokens that define chemical computation operations, e.g., molecule generation operations, molecule filtering operations, or operations that involve executing a chemical computation graph. In response to determining that the sequence of output tokens includes tokens defining a chemical computation operation, the system can perform the chemical computation operation and can determine the response to the user query based at least in part on a result of the chemical computation operation. For instance, the system can provide a set of molecules generated by the chemical computation operation as a response to the user query, or the system can append tokens representing the set of molecules generated by the chemical computation operation to the sequence of output tokens and continue iteratively extending the sequence of output tokens. The system can thus expand the capabilities of the generative neural network to provide responses to complex queries by training and using the generative neural network in a manner that allows the generative neural network to call upon chemical computation operations.

Further, allowing the generative neural network to call upon chemical computation operations as part of generating output sequences of tokens can enable the generative neural network to be implemented with a less complex neural network architecture, or to be trained using less training data, or both, than would otherwise be required. In particular, in the absence of a capability for the generative neural network to call upon chemical operations that are executed by an external computational engine, the generative neural network would be required encode operations approximating chemical computation operations within the trained values of a set of neural network parameters of the generative neural network. Encoding the capacity to perform chemical computation operations in the parameter values of the generative neural network may require a more complex architecture, more training data, or both, and may result in less accurate responses to queries.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
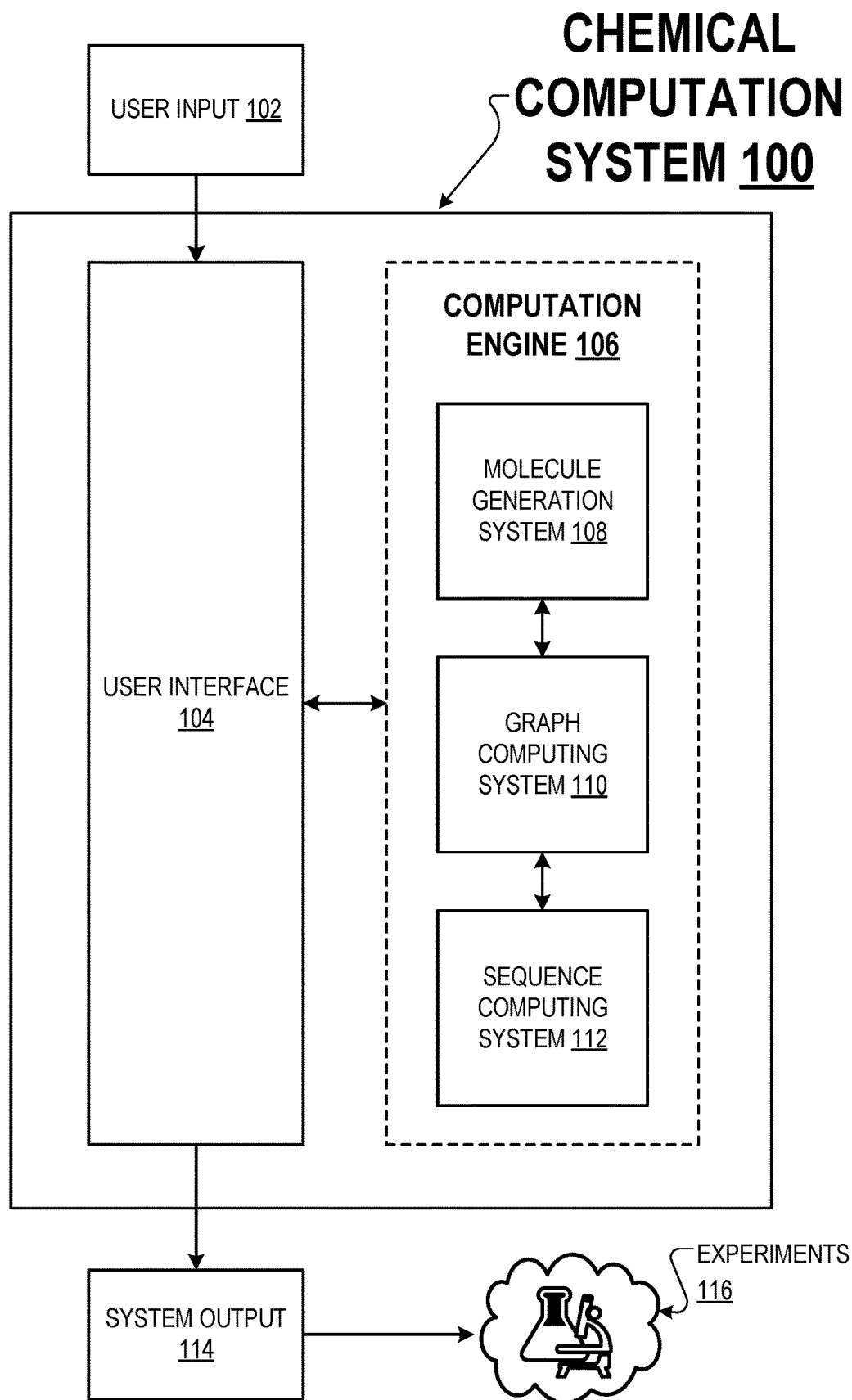
FIG. 1 shows an example chemical computation system.

FIG. 1 shows an example chemical computation system 100. The chemical computation system 100 is an example of a system implemented as computer programs on one or more computers in one or more locations in which the systems, components, and techniques described below are implemented.

The chemical computation system 100 is configured to receive a user input 102 by way of a user interface 104 and to process the user input 102 by a computation engine 106 to generate a system output 114.

The user input 102 can include a request to perform computational operations on molecular data, and the system output 114 can characterize a result of computational operations performed by the chemical computation system 100. A few examples of user inputs 102 and corresponding system outputs 114 are described next.

In some implementations, the user input 102 can define a request for the chemical computation system 100 to generate a collection of candidate molecules that satisfy one or more criteria. A collection of candidate molecules can comprise one or more candidate molecules and, in particular, a plurality of candidate molecules. The chemical computation system 100 can perform computational operations to generate the candidate molecules satisfying the criteria, and the system output 114 can include data defining the collection of candidate molecules (and, in some cases, one or more respective properties of each of the candidate molecules).

In some implementations, the user input 102 can identify a set of input molecules and specify a chemical computation graph which, as will be described in more detail below, defines graph-structured operations to be performed on the set of input molecules to generate a set of output molecules. The chemical computation system 100 can execute the chemical computation graph to generate, as an output of the chemical computation graph, a set of candidate molecules.

The chemical computation system 100 can then provide a system output 114 that includes data defining the set of candidate molecules (and, in some cases, one or more respective properties of each of the candidate molecules).

In some implementations, the user input 102 can include data defining: (i) a chemical structure of each of one or more input molecules, and (ii) a textual query related to the one or more input molecules. The chemical computation system 100 can process the user input 102 to generate a system output 114 that is responsive to the query, e.g., an output that defines one or more candidate molecules satisfying criteria specified by the user input 102. (The system output 114 can further include, in some cases, data defining one or more respective properties of each of the candidate molecules).

The user interface 104 can be any appropriate interface that enables an agent, e.g., a human user an upstream software system, to provide inputs to the chemical computation system 100. For instance, the user interface 104 can include a graphical user interface (GUI) that includes interactive elements such as buttons, drop down menus, drawing tools, text input boxes, and so forth. As another example, the user interface 104 can provide an application programming interface (API) defining a set of rules, protocols, and tools to enable an upstream software system to provide inputs to (and receive outputs from) the chemical computation system 100.

The chemical computation system 100 can provide the system output 114 in any of a variety of possible ways. For instance, the chemical computation system 100 can store the system output 114 in a memory. As another example, the chemical computation system 100 can transmit the system output 114 over a data communications network, e.g., the internet. As another example, the chemical computation system 100 provide a representation of the system output 114 to a user by way of the user interface 104, e.g., by displaying a visual rendering (e.g., in two dimensions or in three dimensions) of one or more molecules included in the system output 114, or by displaying a text-based representation of one or more molecules included in the system output 114 (e.g., by way of a Simplified Molecular Input Line Entry System (SMILES) string).

Molecules generated by the chemical computation system 100 can be used in any of a variety of downstream applications. For instance, molecules generated by the chemical computation system 100 can be physically synthesized using an appropriate chemical synthesis method. Synthesizing a molecule by a chemical synthesis method can include selecting appropriate precursor molecules (e.g., based on factors such as availability, reactivity, and safety), designing reaction conditions (e.g., temperature, pressure, solvents, catalysts), conducting the planned reaction, and purifying the reaction mixture to isolate the desired molecules from by-products, unreacted starting materials, and solvents.

Physical experiments 116 can be performed on a synthesized molecule to determine one or more properties of the synthesized molecule, e.g., one or more of: a binding affinity of the molecule for a binding target; or a solubility of the molecule; or a toxicity of the molecule; or a binding affinity of the molecule for one or more off-target binding sites; or an absorption property of the molecule; or a distribution property of the molecule; or a metabolism property of the molecule; or an excretion property of the molecule.

Any appropriate physical experiments can be performed to determine properties of a synthesized molecule. For instance, determining a binding affinity of a synthesized molecule for a binding target can include preparing solutions of the synthesized molecule at various concentrations, incubating the synthesized molecule with the target under controlled conditions, and using techniques such as surface plasmon resonance (SPR), isothermal titration calorimetry (ITC), or enzyme-linked immunosorbent assay (ELISA) to measure the interaction. As another example, determining a solubility of a synthesized molecule can include selecting appropriate solvents (e.g., water or ethanol), dissolving the molecule in increasing concentrations in the solvent until a saturation point is reached, and using techniques such as high-performance liquid chromatography to measure the concentration of dissolved molecule. As another example, determining a toxicity of a synthesized molecule can include growing suitable cell lines for toxicity testing, treating the cells with various concentrations of the synthesized molecule, and performing assays such as Trypan Blue exclusion to assess cell viability after treatment.

By using a substantially reduced set of molecules such as generated by the chemical computation system 100, in which the number of molecules that are candidates for physical synthesis and testing is significantly reduced, consumption of physical resources, e.g., laboratory resources, that are required for subsequent processing such as physical synthesis, can be reduced.

The chemical computation system 100 can be used as part of a drug discovery pipeline, e.g., to generate and screen large sets of molecules in order to identify molecules for inclusion in drugs, e.g., substances that are predicted to achieve therapeutic effects in subjects, e.g., by curing, treating, or preventing disease in the subject or otherwise enhance physical or mental well-being of the subject. (A drug can be predicted to achieve a therapeutic effect, e.g., if the drug is predicted to bind to a biological target in a manner that modulates the activity of the target and thereby alters cellular processes in a way that counter disease pathology). In some cases, a molecule generated by the chemical computation system 100 can be physically synthesized and then included in a drug to be administered to a subject. By using a substantially reduced set of molecules such as generated by the chemical computation system 100, in which the number of molecules that are candidates for physical synthesis and testing is significantly reduced, resource requirements for subsequent testing, for example in clinical trials, can be reduced.

The computation engine 106 of the chemical computation system 100 can include any combination of one or more of: (i) a molecule generation system 108, (ii) a graph computing system 110, and (iii) a sequence computing system 112, which are each described in more detail next (and throughout this specification).

The molecule generation system 108 is configured to generate a collection of candidate molecules that satisfy one or more molecular criteria (e.g., that are specified by a user input 102), to generate one or more respective molecular scores for each candidate molecule that characterize properties of the candidate molecule, and to filter the set of candidate molecules based on the molecular scores. Example processes for generating and filtering sets of candidate molecules are described in more detail with reference to FIG. 2-FIG. 4.

The graph computing system 110 is configured to execute a chemical computation graph (e.g., that is specified by a user input 102) to generate a set of candidate molecules. The chemical computation graph includes: (i) a set of chemical computation nodes, and (ii) a set of edges. Each chemical computation node is configured to receive a set of input molecules, and to process the set of input molecules in accordance with a sequence of one or more transformation operations associated with the chemical computation node to generate a set of output molecules. Each edge connects a respective first chemical computation node to a respective second chemical computation node and defines that a set of output molecules generated by the first chemical computation node should be provided as an input of input molecules to the second chemical computation node. Example processes for receiving an executing a chemical computation graph are described in more detail with reference to FIG. 5-FIG. 6.

The sequence computing system 112 is configured to receive data defining: (i) a chemical structure of each of one or more input molecules, and (ii) a textual query related to the input molecules. The input molecules and the associated textual query can be specified by a user input 102. The sequence computing system 112 can generate a sequence of input tokens that jointly represent the input molecules and the textual query, and then process the sequence of input tokens using a generative neural network to generate a sequence of output tokens that define data responsive to the textual query. Example processes for generating responses to textual queries related to molecules using a generative neural network are described in more detail with reference to FIG. 7-FIG. 10.

The molecule generation system 108, the graph computing system 110, and the sequence computing system 112 can operate jointly and each of these systems can have the capacity to query (or otherwise interact with) the other systems. For instance, the operations of a chemical computation graph can include molecule generation and molecule filtering operations, and the graph computing system 110 can leverage the molecule generation system 108 to implement these operations during execution of the chemical computation graph. As another example, the sequence computing system 112 can generate, by the generative neural network, a sequence of output tokens that defines a chemical computation graph to be executed as part of generating a response to a query. In this example, the sequence computing system 112 can use the graph computing system 110 to execute the chemical computation graph defined by the output of the generative neural network as part of generating the response to the query. (The chemical computation graph can operate on any appropriate set of input molecules designated by the sequence of output tokes generated by the generative neural network, e.g., molecules represented in the sequence of input tokens, or molecules defined in the sequence of output tokens, or both, as will be described in more detail below with reference to FIG. 7-FIG. 10).

In some cases, the user input 102 can specify input molecules that have been determined by applying physical, experimental processes to a sample, e.g., x-ray crystallography and nuclear magnetic resonance spectroscopy.

Figure 2:
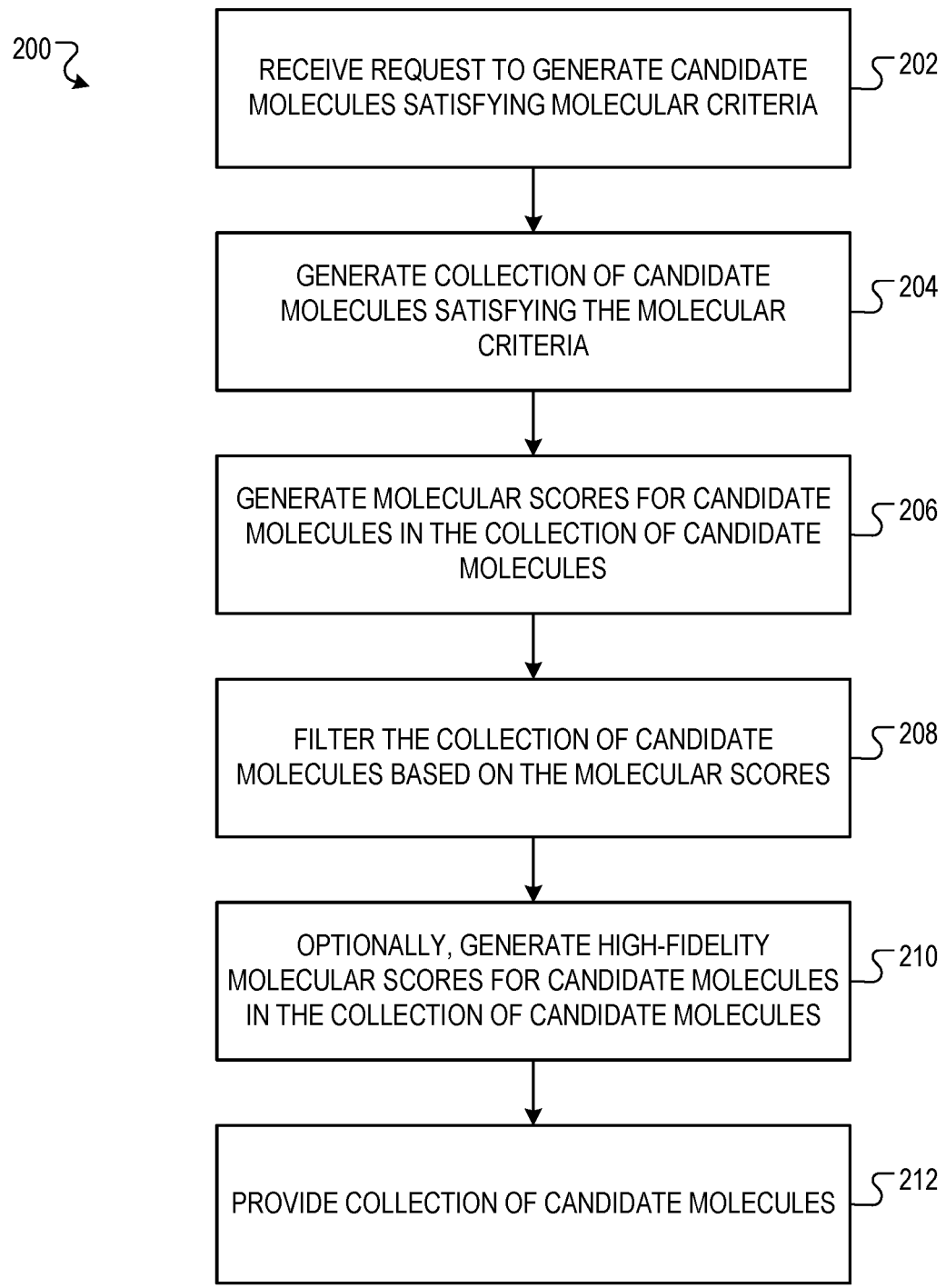
FIG. 2 is a flow diagram of an example process for generating and filtering a set of candidate molecules.

FIG. 2 is a flow diagram of an example process 200 for generating and filtering a set of candidate molecules. For convenience, the process 200 will be described as being performed by a system of one or more computers located in one or more locations. For example, a molecule generation system, e.g., the molecule generation system 108 of FIG. 1, appropriately programmed in accordance with this specification, can perform the process 200.

The system receives a request to generate data identifying candidate molecules satisfying one or more molecular criteria (202). The system can receive the request from any appropriate source, e.g., from a user by way of a user interface, as described in more detail above with reference to FIG. 1.

The molecular criteria can include, e.g., attachment criteria, chemical reaction criteria, or scaffolding criteria. Attachment criteria specify that candidate molecules should be generated by attaching two or more molecules from one or more input sets of molecules, or by replacing one or more portions of a molecule by respective molecular fragments from a set of molecular fragments. Chemical reaction criteria specify that candidate molecules should be generated by chemically reacting one or more molecules from a set of input molecules in accordance with one or more chemical reactions from a set of chemical reactions. Scaffolding criteria specify that candidate molecules should be completions of a scaffold molecule, where the scaffold molecule is represented by a sequence of tokens including one or more masked tokens representing unspecified parts of the scaffold molecule. Attachment criteria, chemical reaction criteria, and scaffolding criteria are each described in more detail next (and throughout this specification).

A few examples of requests to generate candidate molecules that satisfy attachment criteria are described next.

In one example, the system can receive a request to generate data identifying candidate molecules that result from attaching: (i) a first molecule from a first set of molecules, and (ii) a second molecule from a second set of molecules. The first set of molecules and the second set of molecules can be specified by the request. "Attaching" a first molecule to a second molecule can refer to a process of forming one or more chemical bonds (e.g., covalent bonds) between one or more atoms in the first molecule and one or more atoms in the second molecule.

Continuing the previous example, the molecular criteria included in the request can further include data designating one or more attachment points on each molecule in the first set of molecules. In this case, a candidate molecule can be designated as satisfying the molecular criteria if the candidate molecule results from attaching a first molecule from the first set of molecules and a second molecule from the second set of molecules at an attachment point of the first molecule. An "attachment point" on a molecule can refer to a specific site or functional group where another molecule can be chemically bonded.

Continuing the previous example, the molecular criteria included in the request can further include data designating one or more attachment points on each molecule in the second set of molecules. In this case, a candidate molecule can be designated as satisfying the molecular criteria if the candidate molecule results from attaching a first molecule from the first set of molecules and a second molecule from the second set of molecules at respective attachment points of the first molecule and the second molecule.

In another example, the system can receive a request that includes data identifying: (i) a molecule, where one or more portions of the molecule are designated for replacement, and (ii) a set of one or more molecular fragments. In this example, the request can be to generate data identifying candidate molecules that result from replacing each portion of the molecule that is designated for replacement by a respective molecular fragment from the set of molecular fragments. A "molecular fragment" can refer to a molecule or to a portion or part of a molecule e.g., a specific group of atoms or a substructure within a larger molecular entity. Replacing a portion of the molecule with a molecular fragment can refer to substituting a specified specific part or substructure of the molecule with the molecular fragment.

Continuing the previous example, the molecular criteria included in the request can further designate one or more attachment points on the molecule and require that, when replacing a portion of the molecule with a molecular fragment, that the molecular fragment is attached to the molecule at a designated attachment point on the molecule.

The system can provide an interface that enables users to define attachment criteria for generating candidate molecules in any of a variety of possible ways. For instance, as part of specifying attachment criteria, the system can enable a user to specify the molecules included in a set of molecules (e.g., to be attached in accordance with the attachment criteria) by inputting text-based representations of the molecules (e.g., as SMILES strings) or visual representations of the molecules (e.g., by graphically drawing the molecules by way of a graphical user interface). As another example, the system can enable a user to specify molecules by selecting an existing library of molecules, or by selecting a portion of an existing library of molecules, e.g., by selecting all the molecules in a library that satisfy certain criteria, e.g., based on properties of the molecules such as molecular weight, polar surface area, solubility, and so forth. Similarly, the system can enable a user to specify attachment points, portions of molecules designated for replacement, and so forth, using any appropriate interface, e.g., a text-based interface or a graphical interface.

A few examples of requests to generate candidate molecules that satisfy chemical reaction criteria are described next.

In one example, the system can receive a request to generate data identifying candidate molecules that are predicted to result from a chemical reaction involving a molecule from a set of molecules. The set of molecules can be specified in the request.

Continuing the preceding example, the request can further include data selecting one or more chemical reactions, e.g., from a set of possible chemical reactions. In this example, the request can designate that a candidate molecule satisfies the molecular criteria if the candidate molecule is predicted to result from a chemical reaction involving a molecule from the set of molecules, where the chemical reaction is one of the selected chemical reactions.

In another example, the request can be to generate data identifying candidate molecules that are predicted to result from a chemical reaction involving: (i) a first molecule from the first set of molecules, and (ii) a second molecule from a second set of molecules. In this example, the first set of molecules and the second set of molecules can both specified in the request.

Continuing the previous example, the request can further include data identifying one or more chemical reactions, e.g., from a set of possible chemical reactions. In this example, the request can designate that a candidate molecule satisfies the molecular criteria if the candidate molecule is predicted to result from chemically reacting a first molecule from the first set of molecules and a second molecule from the second set of molecules in accordance with one or more of the selected chemical reactions.

Continuing the previous examples, the request can further include data identifying: (i) a reactive portion of each molecule in the first set of molecules, and (ii) a reactive portion of each molecule in the second set of molecules. In this case, the request can designate that a candidate molecule satisfies the molecular criteria if the candidate molecule is predicted to result from chemical reacting the reactive portion of a first molecule in the first set of molecules with the reactive portion of a second molecule in the second set of molecules. For one or more molecules in the first set of molecules or the second set of molecules, the entire molecule can be identified as the reactive portion of the molecule. For one or more molecules in the first set of molecules or the second set of molecules, a proper subset of the atoms and bonds in the molecule can be designated as the reactive portion of the molecule.

In the preceding examples, the set of possible chemical reactions can include one or more of: addition reactions, substitution reactions, elimination reactions, oxidation and reduction reactions, hydrolysis reactions, condensation reactions, polymerization reactions, combination reactions, displacement reactions, acid-base reactions, esterification reactions, redox reactions, or any combination thereof.

The system can provide an interface that enables users to define chemical reaction criteria for generating candidate molecules in any of a variety of possible ways. For instance, the system can provide an interface that enables users to specify sets of molecules, reactive portions of molecules, and so forth, using a text-based interface or a graphical interface as described above with reference to attachment criteria for generating candidate molecules. As another example, the system can enable a user to select chemical reactions from a predefined set of chemical reactions, e.g., by way of drop-down menu or in any other appropriate way.

A few examples of requests to generate candidate molecules that satisfy scaffolding criteria are described next.

In one example, the request can specify a "scaffold" molecule as a sequence of tokens, where one or more of the tokens in the sequence of tokens are "masked" tokens. The request can be to generate one or more candidate molecules that are each represented by a sequence of tokens generated by replacing each masked token in the sequence of token representing the scaffold molecule by one or more non-masked tokens.

More specifically, a molecule can be represented as a sequence of tokens, where each token is drawn from a set of possible tokens. The set of possible tokens can include tokens representing atoms, or bonds, or branches (e.g., from the main chain of the molecule), or ring structures, or charges on atoms, and so forth. Example formats for expressing molecules as sequences of tokens include the Simplified Molecular Input Line Entry System (SMILES) format and the International Chemical Identifier (InChI) format.

The set of possible tokens can further include a "masked" token which represents an unspecified portion of a molecule. That is, in contrast to non-masked tokens that explicitly represent parts of a molecule such as atom, bonds, branches, ring structures, and so forth (as described above), a masked token represents an undefined or unspecified part of the molecule.

Each candidate molecule that is generated by replacing the masked tokens in the scaffold molecule by non-masked tokens thus represents a fully-specified completion of the scaffold molecule, where the unspecified parts of the molecule (represented by the masked tokens) have been replaced by non-masked tokens that define those parts of the molecule.

In another example, in addition to specifying a scaffold molecule, the request can include data that associates one or more respective target molecular fragments with each of one or more of the masked tokens included in the scaffold molecule. In this example, the request can be to generate candidate molecules that, for each of the one or more masked tokens, replace the masked token by one or more non-masked tokens that define a molecular fragment that is an isostere of a target molecular fragment for the masked token. An "isostere" of a target molecular fragment can be another molecular fragment that, when substituted for the target molecular fragment in a molecule, results in a new molecule that is predicted to have similar chemical or physical properties as the original molecule.

In another example, in addition to specifying a scaffold molecule, the request can include data specifying a protein binding site corresponding to a given masked token in the scaffold molecule. In this example, the request can be to generate candidate molecules that each replace the given masked token by one or more non-masked tokens that define a molecular fragment having a conformation that is complementary to the conformation of the protein binding site. A molecular fragment can have a conformation that is "complementary" to that of a protein binding site, e.g., if the molecular fragment has shape complementarity with the protein binding site (such that the molecular fragment has a three-dimensional shape that fits into the protein binding site), or chemical complementarity with the protein binding site (such that chemical properties of the molecular fragment such as charge distribution, hydrophobicity, and hydrogen bonding potential align with those of the protein binding site), or both.

The system can provide an interface that enables users to define scaffolding criteria for generating candidate molecules in any of a variety of possible ways. For instance, the system can enable a user to specify a scaffold molecule, e.g., by selecting a molecule from an existing library of molecules or by defining a molecule using a text-based or graphical user interface. The system can then provide a representation (e.g., a text-based representation or a visual representation) of the scaffold molecule to the user along with an interface that enables the user to select one or more elements (e.g., atoms or bonds) in the scaffold molecule to be masked. The system can then represent the scaffold molecule as a sequence of tokens where each element that the user has selected for masking is represented by a respective masked token.

The system generates a collection of candidate molecules that satisfy the one or more molecular criteria (204). The operations performed by the system to generate the collection of candidate molecules satisfying the molecular criteria depend on the nature of the molecular criteria, e.g., depend on whether the molecular criteria are attachment criteria, or chemical reaction criteria, or scaffolding criteria.

In some cases, the molecular criteria can be attachment criteria, e.g., specifying that candidate molecules should be generated by attaching two or more molecules from one or more sets of input molecules, or by replacing one or more portions of a molecule by respective molecular fragments from a set of molecular fragments, as described above with reference to step 202. In these cases, the system can generate the collection of candidate molecules by systematically enumerating some or all of the molecules that would satisfy the attachment criteria.

For instance, the attachment criteria can specify a first set and a second set of input molecules, optionally along with other data such as attachment points on some or all of the molecules. In this example, the system can systematically enumerate some or all of the molecules that can be generated by attaching molecules from the first of molecules and the second set of molecules (optionally, in accordance with constraints such as using only designated attachment points).

As another example, the attachment criteria can specify one or more portions of a molecule for replacement, and also a set of one or more molecular fragments. In this example, the system can systematically enumerate some or all of the molecules that can be generated by replacing designated portions of the molecule with respective molecular fragments from the set of molecular fragments.

Systematically enumerating the collection of candidate molecules satisfying the attachment criteria is a computationally intensive process well beyond what could be analyzed by a human or solely in the human mind. For instance, the number of molecules satisfying the attachment criteria can increase exponentially with the size of the sets of input molecules to be attached, and can in some cases number in the tens or hundreds of thousands.

In some cases, the molecular criteria can be chemical reaction criteria, e.g., specifying that candidate molecules should be generated by chemically reacting one or more molecules from one or more sets of input molecules in accordance with chemical reactions from a set of chemical reactions, as described above with reference to step 202. In these cases, the system can generate the collection of candidate molecules by systematically determining, for groups of one or more reactant molecules from the sets of input molecules, product molecules that would be generated by chemical reactions involving the group of reactant molecules.

For instance, the chemical reaction criteria can specify a first set and a second set of molecules, optionally along with other data such as specified reactive portions of the molecules and a set of one or more chemical reactions. In this example, the system can systematically evaluate, for each first molecule from the first set of molecules and for each second molecule from the second set of molecules and for each chemical reaction from the set of chemical reactions, a result of chemically reacting the first molecule and the second molecule in accordance with the chemical reaction. Determining the result of chemically reacting one or more molecules can include determining, e.g., a likelihood that the chemical reaction will occur, the yield of the chemical reaction, and the identities of the product molecules generated by the chemical reaction.

The system can determine the result of a specified chemical reaction that involves one or more reactant molecules using any appropriate computational chemistry technique. A few examples of computational chemistry techniques that the system can use for predicting the result of a chemical reaction are described next.

In one example, the system can determine the result of a chemical reaction by performing a computational simulation of the chemical reaction. Performing a computational simulation of a chemical reaction can involve reaction pathway exploration (e.g., exploration of pathways that the reactants could take to transform into products, including calculating transition states and intermediates), solving quantum mechanical equations (e.g., Schrodinger equations to characterize electronic structures of molecules), and performing molecular dynamics simulations (e.g., to characterize the how the molecules behave over time as part of predicting the kinetics and mechanism of the reaction).

In another example, the system can predict the result of a chemical reaction using a product modeling neural network that is configured to process a model input that includes data defining one or more reactant molecules (and optionally additional data, such as data specifying a chemical reaction), in accordance with values of a set of product modeling neural network parameters, to generate a model output that defines one or more predicted product molecules (i.e., that would result from chemically reacting the reactant molecules).

The system can train the product modeling neural network on a set of training examples that each include: (i) a training input that includes data defining one or more reactant molecules (and optionally additional data, such as data specifying a chemical reaction), and (ii) a target output that defines one or more product molecules produced by the chemical reaction of the reactant molecules. The system can train the product modeling neural network, by a machine learning training technique, to optimize an objective function. The objective function can measure, for each training example, a discrepancy between: (i) a predicted output generated by the product modeling neural network by processing the training input of the training example, and (ii) the target output specified by the training example. The objective function can measure a discrepancy between molecules, e.g., between predicted and target product molecules, in any appropriate way, e.g., by representing the predicted and target molecules by respective molecular fingerprints, and then measuring a similarity between the molecular fingerprints, e.g., by a Tanimoto coefficient calculation.

Certain groups of one or more reactant molecules may be unable to undergo a particular chemical reaction, or may have a low likelihood of undergoing the chemical reaction. The system can determine that a group of reactant molecules is unable to chemically react, e.g., through the computational chemistry techniques described above. However, certain computational chemistry techniques may be computationally intensive, and it can be advantageous to avoid the computational burden of applying these computational chemistry techniques to groups of reactant molecules that are unable (or unlikely) to chemically react.

To address this issue, the system can use a use a reactivity neural network to determine, for a group of one or more reactant molecules, a predicted reactivity of the reactant molecules. The predicted reactivity of the reactant molecules can define a predicted likelihood that the reactant molecules will undergo a chemical reaction. The reactivity neural network can be configured to process a network input that characterizes a group of one or more reactant molecules (and, optionally, data identifying a particular chemical reaction), in accordance with values of a set of reactivity neural network parameters, to generate a predicted reactivity of the reactant molecules.

For any group of one or more reactant molecules for which the system predicts a reactivity that is below a threshold, the system can refrain from applying computational chemistry techniques to the reactant molecules to predict a result of chemically reacting the reactant molecules. The system can thus reduce consumption of computational resources (e.g., memory and computing power) by pre-screening groups of reactant molecules to identify those that are unlikely to react, and then refraining from further processing groups of reactant molecules that are unlikely to react by computational chemistry techniques.

In some cases, the molecular criteria can be scaffolding criteria, e.g., specifying that candidate molecules should be completions of a scaffold molecule, as described above with reference to step 202. A few example techniques by which the system can generate collections of candidate molecules that satisfy scaffolding criteria are described next.

In some implementations, the system can generate candidate molecules satisfying the scaffolding criteria using an autoregressive molecular generation neural network. An example process for generating candidate molecules satisfying scaffolding criteria using an autoregressive molecular generation neural network is described in more detail with reference to FIG. 3.

In some implementations, the system can generate candidate molecules satisfying the scaffolding criteria by, for each candidate molecule, generating the candidate molecule by replacing the masked tokens in the sequence of masked tokens representing the scaffold molecule by non-masked tokens representing respective molecular fragments selected from a set of molecular fragments. More specifically, the system can generate candidate molecules by systematically enumerating molecules that are generated by replacing masked tokens in the scaffold molecule by molecule fragments from the set of molecule fragments.

The set of molecular fragments that provides the molecular fragments used for completing the scaffold molecule can be generated in any appropriate way.

For instance, the set of molecular fragments can be generated at least in part by fragmenting each molecule in a predefined library of molecules. "Fragmenting" a molecule can involve systematically breaking the chemical bonds in the molecule to create smaller, chemically stable molecule fragments.

As another example, the system can generate the set of molecular fragments by systematically enumerating molecular fragments satisfying a set of generation criteria. The set of generation criteria can include size constraints (e.g., setting limits on the number of atoms or the molecular weight), functional group constraints (e.g., requiring that specific functional groups are included or excluded), synthetic accessibility constraints (e.g., requiring that the molecular fragments can be feasibly synthesized), and so forth.

As another example, molecular fragments in the set of molecular fragments can be generated by a generative neural network that has been trained on a library of molecular fragments and can generate samples from a space of possible molecular fragments. The generative neural network can be implemented, e.g., as a generative adversarial network (GAN), or as a variational autoencoder (VAE)-based generative model, or as a diffusion neural network model, or as any other appropriate generative neural network model.

The collection of candidate molecules can include any appropriate number of candidate molecules, e.g., at least 1000 candidate molecules, or at least 10,000 candidate molecules, or at least 100,000 candidate molecules. Further the system can, in some cases, generate the collection of candidate molecules in under an hour, or in under a minute, or in under a second.

The system generates, for candidate molecule in the collection of candidate molecules, one or more molecular scores that characterize one or more properties of the candidate molecule (206).

For instance, for each candidate molecule, the system can generate molecular scores characterizing one or more of: a binding affinity of the candidate molecule for a binding target; a solubility of the candidate molecule; a toxicity of the candidate molecule; a binding affinity of the candidate molecule for one or more off-target binding sites; an absorption property of the candidate molecule; a distribution property of the candidate molecule; a metabolism property of the candidate molecule; an excretion property of the candidate molecule; a molecular weight property of the candidate molecule; or a topological polar surface area of the candidate molecule.

The system can determine the molecular scores for the candidate molecules using any appropriate computational techniques, e.g., molecular docking, quantitative structure-activity relationship (QSAR) models, machine learning models, physics-based molecular dynamics simulations, pharmacophore modeling, or physiochemical property calculations.

In a particular example, for each candidate molecule, the system can generate a molecular score defines a predicted property of the candidate molecule (e.g., toxicity, solubility, etc.) using a scoring machine learning model. For instance, for each candidate molecule, the system can process a model input that characterizes the candidate molecule using the scoring machine learning model, in accordance with values of a set of scoring machine learning model parameters, to generate a predicted property of the candidate molecule.

The system can train the scoring machine learning model on a set of training examples that each include: (i) a training input that includes data characterizing an input molecule, and (ii) a target output that defines an actual property of the input molecule. The system can train the scoring machine learning model, by a machine learning training technique, to optimize an objective function. The objective function can measure, for each training example, a discrepancy between: (i) a predicted property generated by the scoring machine learning model by processing the training input of the training example, and (ii) an actual property of the molecule as defined by the target output specified by the training example. The objective function can measure a discrepancy between a predicted property and an actual property of a molecule in any appropriate way, e.g., by an absolute error or a squared error between the predicted value and the actual value of the property.

Performing a physics-based molecular dynamics simulation to determine a molecular score characterizing a property of a molecule can include: obtaining data defining an atomic-level structure of the molecule; selecting an appropriate force field that describes interactions between atoms (e.g., bonded and non-bonded interactions); parametrizing the simulation, e.g., by assigning values for bond lengths, angles, dihedrals, van der Waals forces, and electrostatic interactions; integrating equations of motion over time using a suitable algorithm (e.g., leapfrog integration); collecting trajectory data over time, including the positions, velocities, and possibly energies of the atoms being simulated; and analyzing the trajectory data to extract the property of interest.

The system filters the collection of candidate molecules, based on the molecular scores, to remove multiple candidate molecules from the collection of candidate molecules (208). The collection of candidate molecules can include any appropriate number of candidate molecules, e.g., at least 1000 candidate molecules, or at least 10,000 candidate molecules, or at least 100,000 candidate molecules, and the system can filter any appropriate fraction of the candidate molecules, e.g., by removing at least 10%, or at least 50%, or at least 90%, or at least 99% of the candidate molecules in the collection of candidate molecules.

The system can filter the collection of candidate molecules in accordance with any appropriate filtering criteria. A few examples of possible filtering criteria are described next.

In one example, for one or more molecular scores, the system can associate the molecular score with a predefined range of tolerable values. The system can determine, for each candidate molecule, that the candidate molecule should be filtered (removed) from the set of candidate molecules if the value of the molecular score for the candidate molecule is outside the range of tolerable values for the molecular score. Thus, for instance, the system can define a range of tolerable values for a toxicity molecular score, and can filter any candidate molecules having a toxicity that is above an upper bound of the range of tolerable toxicity values from the collection of candidate molecules.

As another example, for one or more molecular scores, the system can determine a ranking of the candidate molecules in the collection of candidate molecules based on values of the molecular score for the candidate molecules. For instance, the system can rank the collection of candidate molecules from highest-to-lowest values of the molecular score, or from lowest-to-highest values of the molecular score. The system can then determine, for each candidate molecule, that the candidate molecule should be filtered (removed) from the set of candidate molecules if the candidate molecule is ranked outside the top-N (or lowest-N) from among the collection of candidate molecules based on the ranking of the candidate molecules according to values of the molecular score (where N is any appropriate positive integer numerical value, e.g., 100 or 1000 or 10,000). Thus, for instance, the system can rank the candidate molecules based on their predicted binding affinity for a binding site, and can filter any candidate molecules that are not included in the top-N (or lowest-N) candidate molecules based on a ranking of the candidate molecules according to their predicted binding affinity for the binding site.

In some implementations, the system maintains an auxiliary set of molecules, referred to for convenience as a set of "filtering" molecules, and uses the set of filtering molecules as part of filtering the collection of candidate molecules. More specifically, the system can determine, for each candidate molecule, whether the candidate molecule satisfies a matching criterion with each filtering molecule in the set of filtering molecules. The system can then determine whether to filter the candidate molecule based at least in part on whether the candidate molecule satisfies the matching criterion with each filtering molecule in the set of filtering molecules.

The system can evaluate whether a candidate molecule satisfies a matching criterion with a filtering molecule in any of a variety of possible ways. A few example techniques for evaluating a matching criterion between a candidate molecule and a filtering molecule are described next.

In one example, to evaluate a matching criterion for a candidate molecule and a filtering molecule, the system can determine a chemical structure similarity between the candidate molecule and the filtering molecule. For instance, the system can generate respective molecular fingerprints for the candidate molecule and the filtering molecule. A molecular fingerprint for a molecule can be a tensor of numerical values that represents the presence or absence of certain chemical features or patterns within the molecule, e.g., features such as the presence of specific atoms (e.g., carbon, nitrogen, oxygen, and so forth), the presence of specific functional groups (e.g., hydroxyl, carbonyl, or amine functional groups), the presence of certain structures (e.g., rings, double bonds, and so forth), and the presence of topological features characterizing connectivity or relationships between atoms in the molecule. The system can compute a measure of similarity between the molecular fingerprints of the candidate molecule and the filtering molecule, and then determine that the matching criterion is satisfied, e.g., if the measure of similarity exceeds a threshold. The measure of similarity can be determined, e.g., using a Tanimoto coefficient, a cosine similarity, a Hamming distance, or a Euclidean distance.

In another example, to evaluate a matching criterion for a candidate molecule and a filtering molecule, the system can determine a binding affinity between the candidate molecule and the filtering molecule, e.g., using an appropriate computational technique such as molecular docking or machine learning models trained to predict binding affinity. The system can determine that the matching criterion is satisfied, e.g., if the binding affinity between the candidate molecule and the filtering molecule satisfies (e.g., exceeds) a threshold.

A few example techniques by which the system can determine whether to filter a candidate molecule based on whether the candidate molecule satisfies a matching criterion with each filtering molecule in the set of filtering molecules are described next.

In some implementations, the system can determine that a candidate molecule should be filtered in response to determining that the candidate molecule satisfies the matching criterion with at least one filtering molecule in the set of filtering molecules.

For instance, the matching criterion may be based on chemical structure similarity (as described above), and the set of filtering molecules may include molecules that are known to have undesirable properties (e.g., high toxicity). Candidate molecules that are structurally similar to the filtering molecules may have an increased likelihood of having undesirable properties, and thus filtering the candidate molecules using the set of filtering molecules can have the effect of removing molecules that have an increased likelihood of having undesirable properties from the collection of candidate molecules.

As another example, the matching criterion may be based on binding affinity (as described above), and the set of filtering molecules may include molecules that include off-target binding sites. An off-target binding site can refer to a specific region or structure where a substance (e.g., a drug) can bind but that is not the primary or intended interaction for the substance. Candidate molecules that have a high binding affinity for off-target binding sites, as included in molecules in the set of filtering molecules, can thus be filtered from the set of candidate molecules.

In some implementations, the system can determine that the a candidate molecule should be filtered in response to determining that the candidate molecule does not satisfy the matching criterion with any of the filtering molecules in the set of filtering molecules.

For instance, the matching criterion may be based on chemical structure similarity (as described above), and the set of filtering molecules may include molecules that are known to have desirable properties, e.g., drug-like properties in terms of bioavailability, molecular weight, solubility, stability, and so forth. Candidate molecules that are structurally similar to the filtering molecules may thus have an increased likelihood of having desirable properties, and thus filtering the candidate molecules using the set of filtering molecules can have the effect of removing molecules with a low likelihood of having desirable properties (e.g., drug-like properties) from the collection of candidate molecules.

As another example, the matching criterion may be based on binding affinity (as described above), and the set of filtering molecules may include molecules that have on-target binding sites, e.g., binding sites where a drug is intended to bind in order to exert its therapeutic effect. Candidate molecules having a low binding affinity for on-target binding sites, as included in molecules in the set of filtering molecules, can thus be filtered from the set of candidate molecules.

Optionally, after filtering the collection of candidate molecules, the system can generate one or more respective "high-fidelity" molecular scores for each candidate molecule in the collection of candidate molecules (210). The system can generate the high-fidelity molecular scores using high-fidelity scoring models which are different from the scoring models used to generate molecular scores (as described at step 206) that are used for filtering the collection of candidate molecules. In particular, the high-fidelity scoring models are predicted to be more accurate than the scoring models that generated the molecular scores used for filtering the collection of candidate molecules. However, the high-fidelity scoring models may be more computationally complex and intensive than the scoring models used for filtering the collection of candidate molecules, and generating high-fidelity scores for all the candidate molecules included in the collection of candidate molecules prior to filtering may be computationally infeasible. An example process for generating high-fidelity molecular scores using high-fidelity scoring models, and using the high-fidelity molecular scores for training the scoring models used at step 206, is described in more detail with reference to FIG. 4.

The system can output a representation of the collection of candidate molecules (212). For instance, as described above, the system can provide a (visual or text-based) representation of the candidate molecules in the collection of candidate molecules to a user by way of a user interface, or the system can store data defining the collection of candidate molecules in a memory, or the system can transmit data defining the collection of candidate molecules over a data communication network, e.g., the internet, e.g., for presentation by or storage in a different system.

In addition to outputting the collection of candidate molecules, the system can further output data characterizing the candidate molecules, e.g., by providing one or more molecular scores for each candidate molecule. A molecular score for a candidate molecule can characterize a property of the candidate molecule, e.g., binding affinity, solubility, toxicity, and so forth. In implementations where the system generates high-fidelity molecular scores for the candidate molecules in the collection of candidate molecules, as described at step 210, the system can provide data defining the high-fidelity molecular scores for the candidate molecules.

Optionally, the system can rank the collection of candidate molecules in an accordance with the values of a molecular score. For instance, the system can rank the candidate molecules from high-to-low, or from low-to-high, in relation to the molecular score. The molecular score can characterize, e.g., binding affinity for a binding target, stability, toxicity, or any other appropriate property. The system can present a representation of the collection of candidate molecules in a manner that reflects the ranking, e.g., by displaying the collection of candidate molecules as a list, where the list is ordered in accordance with the ranking, e.g., with the highest-ranked candidate molecules at the top of the list. In implementations where the system generates high-fidelity molecular scores for the candidate molecules in the collection of candidate molecules, as described at step 210, the system can rank the collection of candidate molecules in accordance with the values of the high-fidelity molecular score, e.g., to achieve greater accuracy in the ranking.

The system can enable a user to continue to transform and filter the output collection of candidate molecules. For instance, the system can provide, to the user, an interface that enables the user to specify one or more new sorting or filtering criteria for the collection of candidate molecules based on the molecular scores for the candidate molecules. As another example, the system can enable the user to specify new molecular criteria for generating new candidate molecules that are based at least in part on the output collection of candidate molecules, and then repeat the steps of the process 200 to generate new candidate molecules that satisfy the new molecular criteria. The process 200 can thus be an iterative process of refining collections of candidate molecules, e.g., as part of drug discovery pipeline.

In some cases, one or more candidate molecules in the collection of candidate molecules are selected for physical synthesis. The selected candidate molecules can then be physically synthesized, experimentally tested, and in some cases, included in drugs to be administered to subjects to achieve a therapeutic effect, as described above with reference to FIG. 1.

Figure 3:
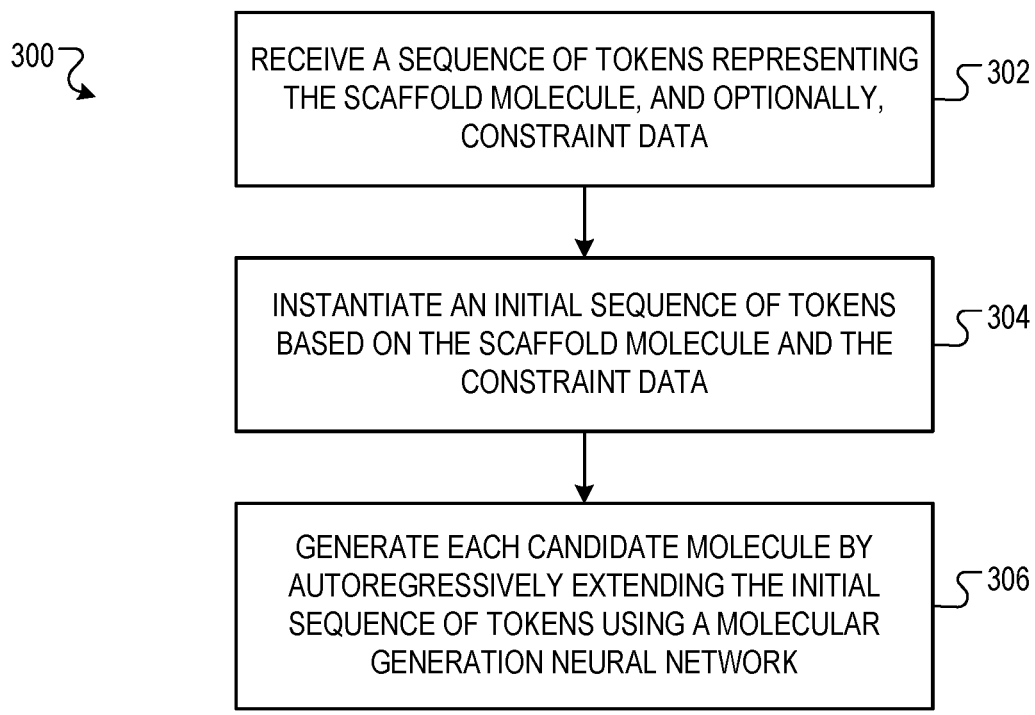
FIG. 3 is a flow diagram of an example process for generating candidate molecules satisfying scaffolding criteria using an autoregressive molecular generation neural network.

FIG. 3 is a flow diagram of an example process 300 for generating candidate molecules satisfying scaffolding criteria using an autoregressive molecular generation neural network. For convenience, the process 300 will be described as being performed by a system of one or more computers located in one or more locations. For example, a molecule generation system, e.g., the molecule generation system 108 of FIG. 1, appropriately programmed in accordance with this specification, can perform the process 300.

The system receives a sequence of tokens, including one or more masked tokens, representing the scaffold molecule (302). Optionally, the system may receive additional constraint data defining criteria to be satisfied for a candidate molecule to be a valid completion of the scaffold molecule. For instance, the constraint data can associate data defining a protein binding site to a masked token, and require that the masked token is replaced by a molecular fragment that is complementary to the conformation of the protein binding site. As another example, the constraint data can associate one or more target molecular fragments with each of one or more masked tokens in the scaffold molecule, and require that each masked token is replaced by a molecular fragment that is an isostere of a target molecular fragment for the masked token.

The system instantiates a current sequence of tokens (304). The current sequence of tokens includes: (i) a sequence of tokens representing some or all of the tokens in the scaffold molecule, and (ii) one or more sequences of tokens representing the constraint data.

For instance, for constraint data that associates a protein binding site to a masked token, the current sequence of tokens can include a sequence of tokens representing the protein binding site, e.g., a sequence of tokens defining a SMILES string or InChI string that defines the protein binding site.

As another example, for constraint data that associates each of one or more masked tokens in the scaffold molecule with one or more target molecular fragments, the current sequence of tokens can include a respective sequence of tokens representing each target molecular fragment, e.g., as a SMILES string or InChI string. In some cases, each sequence of tokens representing a respective target molecular fragment can further include one or more tokens that associates the target molecular fragment with a position of the corresponding masked token in the sequence of tokens representing the scaffold molecule.

To generate each candidate molecule, the system autoregressively extends the current sequence of tokens (starting from the initial sequence of tokens determined at step 304), one token at a time and using the molecular generation neural network, until a termination criterion is satisfied (306).

More specifically, at each extension iteration in a sequence of extension iterations, the system processes a network input that includes the current sequence of tokens, using the molecular generation neural network and in accordance with values of a set of molecular generation neural network parameters, to generate a score distribution over a set of non-masked tokens. The set of non-masked tokens can include tokens representing, e.g., atoms, bonds, branches, ring structures, and so forth. In some cases, at one or more extension iterations where the system is extending the current sequence of tokens to generate a token to replace a masked token, the current sequence of tokens includes each token that precedes the masked token in the sequence of tokens representing the scaffold molecule.

At each extension iteration, the system then selects a non-masked token from the set of non-masked tokens in accordance with the score distribution over the set of non-masked tokens. For instance, the system can randomly sample a non-masked token from the set of non-masked tokens in accordance with the score distribution over the set of non-masked tokens, e.g., from a probability distribution that is generated by processing the score distribution over the set of non-masked tokens using a soft-max function.

At each extension iteration, the system appends the selected non-masked token to the current sequence of tokens, and then evaluates whether a termination criterion is satisfied. The termination criterion can be, e.g., that the selected non-masked token is a predefined "end-of-sequence" (EOS) token, or that a predefined maximum number of extension iterations have been performed. In response to determining that the termination criterion is not satisfied, the system can proceed to the next extension iteration. In response to determining that the termination criterion is satisfied, the system can terminate the process of extending the current sequence of tokens and designate the current sequence of tokens as the final sequence of tokens.

The final sequence of tokens can represent the candidate molecule. In particular, the final sequence of tokens can include, for each masked token in the original sequence of tokens representing the scaffold molecule, a respective sequence of one or more non-masked tokens that replace the masked token.

The process of autoregressively extending an initial sequence of tokens to generate a final sequence of tokens that represents a completion of the scaffold molecule includes steps that involve randomness (e.g., randomly sampling a non-masked token at each extension iteration). The system can autoregressively extend the initial sequence of tokens to generate a respective final sequence of tokens any desired number of times, and each final sequence of tokens represents a respective (potentially different) completion of the scaffold molecule. The system can thus generate multiple candidate molecules by repeatedly autoregressively extending an initial sequence of tokens to generate a final sequence of tokens that defines a new candidate molecule.

The system can train the molecular generation neural network on a set of training examples to perform an unmasking task. More specifically, each training example can include: (i) a partially-masked representation of a training molecule as a sequence of tokens, wherein each one or more of the tokens are masked tokens, and (ii) a non-masked representation of the training molecule as the sequence of tokens, where each token in a non-masked token. Optionally, one or more training examples can include constraint data, as described above.

The system can train the molecular generation neural network on a training example by training the molecular generation neural network to process the partially-masked representation of the training molecule (and, optionally, any constraint data) to generate the non-masked representation of the training molecule.

More specifically, for each training example, the system can determine: (i) an initial sequence of tokens that defines the partially masked training molecule and any constraint data (as described above), and (ii) a target sequence of tokens that defines a non-masked version of the training molecule. The system can use the molecular generation neural network to iteratively extend the initial sequence of tokens, and at each extension iteration, can generate a score distribution over a set of non-masked tokens. The system can train the molecular generation neural network to optimize an objective function that, for each extension iteration, measures an error (e.g., a cross-entropy error) between: (i) the score distribution generated over the set of non-masked tokens at the extension iteration, and (ii) a non-masked token at a corresponding position in the target sequence of tokens.

The molecular generation neural network can include any appropriate neural network architecture that enables the molecular generation neural network to perform its described functions. For instance, the molecular generation neural network can be implemented as a neural network that includes one or more self-attention neural network layers, e.g., as a transformer decoder. As another example, the molecular generation neural network can be implemented as a recurrent neural network that includes one or more recurrent neural network layers, e.g., long short-term memory (LSTM) neural network layers.

Figure 4:
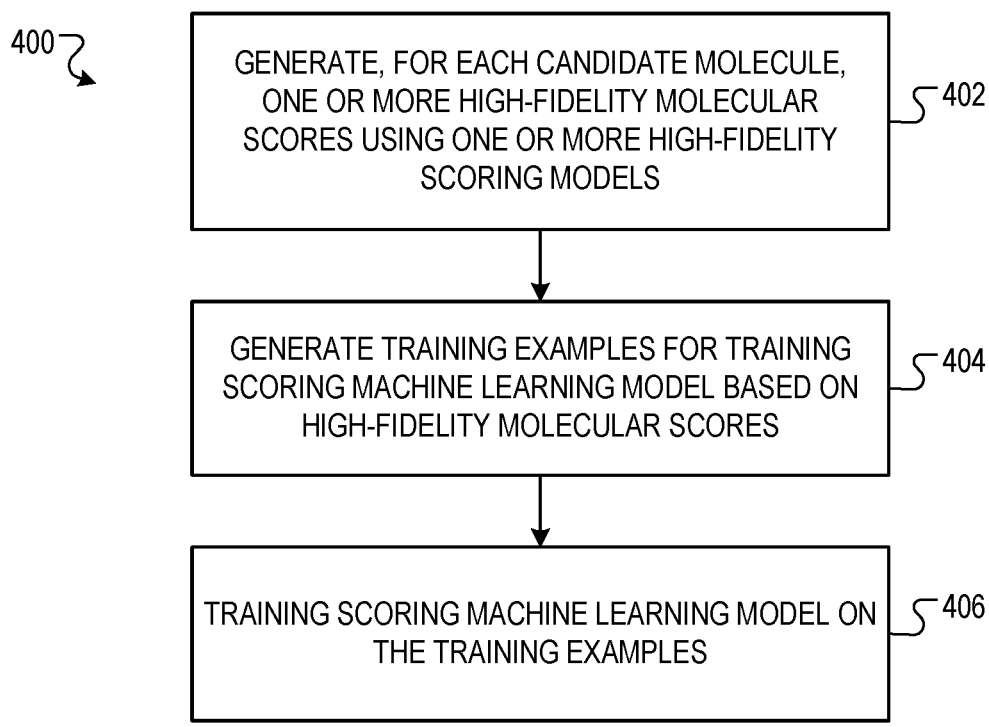
FIG. 4 is a flow diagram of an example process for generating high-fidelity molecular scores using high-fidelity scoring models and using the high-fidelity molecular scores for machine learning training.

FIG. 4 is a flow diagram of an example process 400 for generating high-fidelity molecular scores using high-fidelity scoring models and using the high-fidelity molecular scores for machine learning training. For convenience, the process 400 will be described as being performed by a system of one or more computers located in one or more locations. For example, a molecule generation system, e.g., the molecule generation system 108 of FIG. 1, appropriately programmed in accordance with this specification, can perform the process 400.

The system generates, for each candidate molecule in the collection of candidate molecules, one or more high-fidelity molecular scores for the candidate molecule using one or more respective high-fidelity scoring models (402). In more detail, each high-fidelity scoring model is configured to process a model input that characterizes a candidate molecule to generate a high-fidelity estimate of a molecular score for the candidate molecule. Each high-fidelity scoring model is referred to as "high-fidelity" because it is predicted to be more accurate than a corresponding "low-fidelity" scoring model that generates a low-fidelity estimate of the same molecular score.

The system can use the low-fidelity scoring models to generate low-fidelity estimates of molecular scores for filtering the collection of candidate molecules (as described at step 206 of FIG. 2), and then provide the remaining candidate molecules in the collection of candidate molecules to be re-scored using the high-fidelity scoring models. The high-fidelity scoring models may be significantly more computationally intensive than the low-fidelity scoring model, and thus running the high-fidelity scoring models on the entire collection of candidate molecules, prior to the collection of candidate molecules being filtered, may be computationally infeasible.

The identifiers "high-fidelity" and "low-fidelity" are used to conveniently identify and distinguish different scoring models, and do not require that a scoring model designated as being high-fidelity necessarily produces a more accurate estimate of a molecular score in every instance than a scoring model designated as being low-fidelity. Rather, a scoring model can be designated as being high-fidelity if the scoring model is predicted to be more accurate (e.g., in the aggregate, e.g., on average) than a corresponding scoring model designated as being low-fidelity.

A high-fidelity scoring model may be predicted to achieve a higher accuracy than a low-fidelity scoring model for a variety of reasons. For instance, the high-fidelity scoring model may have a greater number of model parameters than the low-fidelity scoring model, or the high-fidelity scoring model may perform a higher number of arithmetic operations than the low-fidelity scoring model as part of generating as estimate of a molecular score, or the high-fidelity scoring model may require a greater amount of memory in order to execute its operations than the low-fidelity scoring model.

Each high-fidelity scoring model (and each corresponding low-fidelity scoring model, as used at step 206 of the process 200 described with reference to FIG. 2) can be implemented using as any appropriate respective computational model, e.g., as a molecular docking model, or a QSAR model, or a machine learning model, or a physics-based molecular dynamics simulation model, or any combination thereof, and so forth.

The system can provide the high-fidelity molecular scores as output data along with the collection of candidate molecules, as described with reference to step 212 of FIG. 2. The high-fidelity molecular scores can further be used, e.g., for ranking the candidate molecules in the collection of candidate molecules as part of outputting the collection of candidate molecules.

In some cases, as will be described in more detail next with reference to steps 404-406, a low-fidelity scoring model can be a machine learning model (referred to for convenience as a scoring machine learning model, which can be implemented, e.g., as a neural network model, or as any other appropriate type of machine learning model), as described with reference to FIG. 2. In this case, the high-fidelity molecular scores generated by a corresponding high-fidelity scoring model (i.e., that generates estimates of the same molecular score as the scoring machine learning model) can be used for training the scoring machine learning model to generate more accurate estimates of the molecular score.

To this end, the system can generate a set of training examples for training the scoring machine learning model (404). Each training example corresponds to a respective candidate molecule and includes: (i) a representation of the candidate molecule, and (ii) a high-fidelity molecular score generated by the high-fidelity scoring model for the candidate molecule.

The system trains the scoring machine learning model on the set of training examples (406). In particular, the system trains the scoring machine learning model to optimize an objective function that, for each training example, measures a discrepancy (e.g., a squared-error or absolute error) between: (i) a predicted molecular score generated by the scoring machine learning model by processing the representation of the candidate molecule specified by the training example, and (ii) the high-fidelity molecular score specified by the training example. That is, for each training example, the system can train the scoring machine learning model to process the representation of the candidate molecule of the training example to generate a molecular score for the candidate molecules that matches the high-fidelity molecular score of the training example.

The system can thus leverage the complementary properties of a high-fidelity scoring model and a low-fidelity scoring model to reduce consumption of computational resources while increasing prediction accuracy. In particular, the system can initially screen and filter the collection of candidate molecules using the low-fidelity scoring model, and then re-score the remaining molecules using the high-fidelity scoring model. By reducing the number of predictions made by the high-fidelity scoring model, the system can reduce consumption of computational resources, e.g., memory and computing power. Further, the system can use the high-fidelity molecular scores generated by the high-fidelity scoring model as training data for training the low-fidelity scoring model and thus improving the robustness and accuracy of the low-fidelity scoring model.

Figure 5:
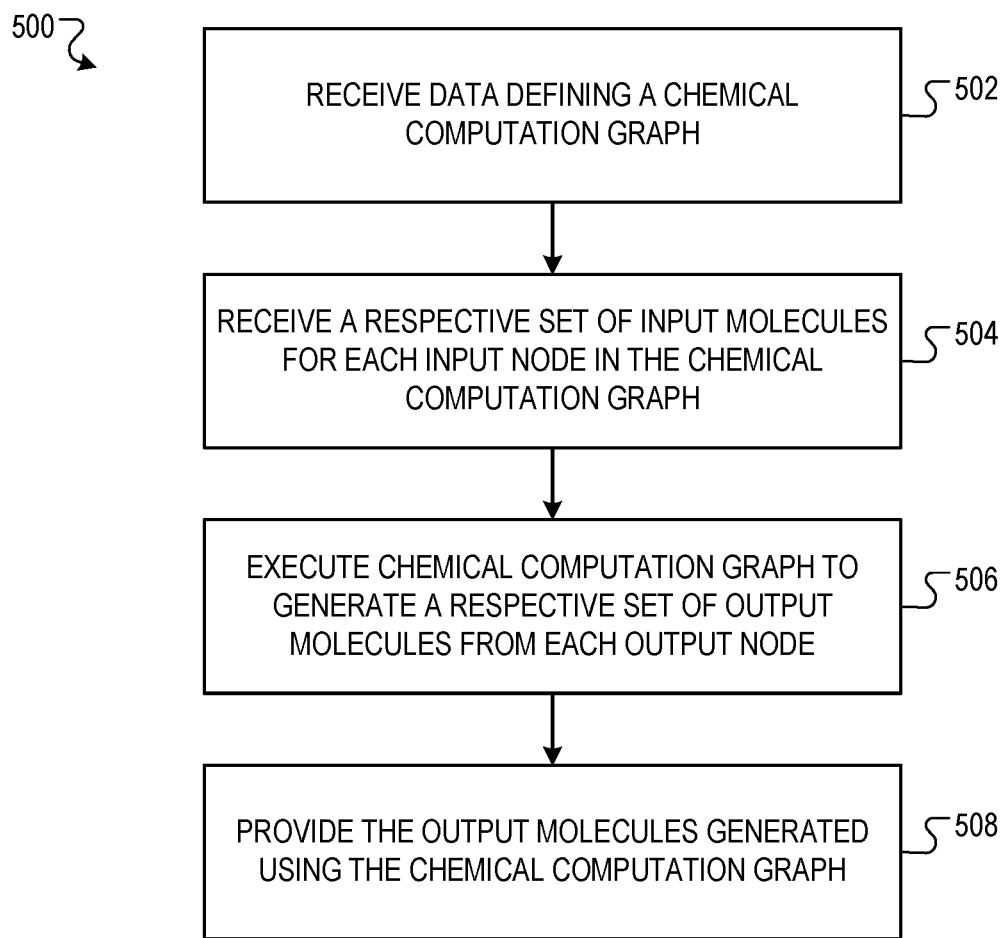
FIG. 5 is a flow diagram of an example process for generating candidate molecules using a chemical computation graph.

FIG. 5 is a flow diagram of an example process 500 for generating candidate molecules using a chemical computation graph. For convenience, the process 500 will be described as being performed by a system of one or more computers located in one or more locations. For example, a graph computing system, e.g., the graph computing system 110 of FIG. 1, appropriately programmed in accordance with this specification, can perform the process 500.

The system receives data defining a chemical computation graph (502). The chemical computation graph is a directed graph that includes: (i) a set of chemical computation nodes, and (ii) a set of edges.

Each chemical computation node is configured to receive a set of input molecules, and to process the set of input molecules in accordance with a sequence of one or more transformation operations associated with the chemical computation node to generate a set of output molecules.

Each edge in the chemical computation graph connects a respective first chemical computation node to a respective second chemical computation node and defines that a set of output molecules generated by the first chemical computation node should be provided as a set of input molecules to the second chemical computation node. The chemical computation graph is a directed graph, e.g., such that each edge in the chemical computation graph is a directed edge that routes the output of one chemical computation node to be the input of another chemical computation node.

Generally, the chemical computation graph is a weakly connected graph, e.g., such that there exists a path (without reference to the directions of the edges) between every pair of nodes in the graph.

The chemical computation graph can include any appropriate number of nodes and any appropriate number of edges. For instance, the chemical computation graph may include at least 3 nodes, or at least 5 nodes, or at least 10 nodes, or at least 100 nodes, and can include at least a number of number sufficient for the chemical computation graph to be weakly connected.

The chemical computation graph can be characterized by a non-linear configuration, e.g., by inclusion of edges that connect one chemical computation node to two or more respective other nodes (thus forming divergent paths). The chemical computation graph can thus represent a complex, interrelated graph of chemical computation operations (as opposed to, e.g., a simple linear sequence of operations).

The chemical computation graph can include one or more cyclical subgraphs. Each cyclical subgraph includes a set of one or more chemical computation nodes and a set of one or more edges that form a cycle in the larger chemical computation graph. More specifically, the set of nodes in a cyclical subgraph can be ordered in a sequence such that: (i) for each node before the last node in the sequence, the node is connected by an edge to the next node in the sequence, and (ii) the last node in the sequence is connected by an edge to the first node in the sequence.

The chemical computation graph can include one or more nodes designated as input nodes. Each input node is configured to receive a set of molecules specified by a user, e.g., as opposed to only receiving molecules that are internally generated in the chemical computation graph, e.g., as the output of another node in the chemical computation graph. The chemical computation graph can include any appropriate number of input nodes, e.g., 1, 5, or 10 input nodes.

The chemical computation graph can include one or more nodes designated as output nodes. The output molecules generated by the output nodes during execution of the chemical computation graph collectively define the set of candidate molecules generated by the chemical computation graph. The chemical computation graph can include any appropriate number of output nodes, e.g., 1, 5, or 10 output nodes.

The chemical computation graph can include one or more chemical computation nodes that are each configured to respective sets of input molecules from multiple sources. For instance, the chemical computation graph can include a chemical computation node that is configured to receive, as input, a respective set of output molecules generated by each of multiple other chemical computation nodes in the chemical computation graph.

Each chemical computation node in the chemical computation graph is associated with a respective sequence of one or more transformation operations. The sequence of transformation operations can include: one or more molecule generation operations; or one or more molecule filtering operations; or both.

For instance, the sequence of transformation operations can include a molecule generation operation followed by a molecule filtering operation. As another example, the sequence of transformation operations can include a molecule filtering operation followed by a molecule generation operation.

As another example, the sequence of transformation operations can include a molecule generation operation followed by a molecule filtering operation followed by another molecule generation operation.

More generally, for a sequence of transformation operations implemented by a chemical computation node, the transformation operation can operate on some or all of the input molecules in the set of input molecules provided to the chemical computation node. Each transformation operation after the first transformation operation in the sequence of transformation operations can operate on a set of molecules generated by the preceding transformation operation in the sequence of transformation operations. The set of molecules generated by the final transformation operation in the sequence of transformation operations can define the set of output molecules generated by the chemical computation node.

A molecule generation operation refers to an operation that is parametrized by a set of molecular generation criteria and that operates on a set of input molecules to generate a set of output molecules, where each output molecule satisfies the set of molecular generation criteria.

Examples of molecular generation criteria include: attachment criteria, chemical reaction criteria, and scaffolding criteria. Attachment criteria specify that output molecules should be generated by attaching two or more molecules from one or more input sets of molecules, or by replacing one or more portions of a molecule by respective molecular fragments from a set of molecular fragments. Chemical reaction criteria specify that output molecules are generated by chemically reacting one or more molecules from a set of input molecules in accordance with one or more chemical reactions from a set of chemical reactions. Scaffolding criteria specify that output molecules should be generated as completions of a scaffold molecule, where the scaffold molecule is represented by a sequence of tokens including one or more masked tokens representing unspecified parts of the scaffold molecule.

Attachment criteria, chemical reaction criteria, and scaffolding criteria are described in detail with reference to step 202 of FIG. 2.

A molecule filtering operation refers to an operation that is parameterized by a set of filtering criteria and that operates on a set of input molecules to filter (remove) any molecules from the set of input molecules that satisfy one or more of the filtering criteria.

In some cases, to implement a molecule filtering operation, a chemical computation node generates, for each input molecule in a set of input molecules, one or more respective molecular scores that each characterize a respective property of the input molecule. Generating molecular scores for candidate molecules is described in detail with reference to step 206 of FIG. 2. The system can then filter the set of input molecules using filtering criteria that are based on the molecular scores for the input molecules. Example techniques for filtering a set of molecules based on molecular scores associated with molecules in the set of molecules is described in detail with reference to step 208 of FIG. 2.

In some cases, the system can implement a filtering operation with reference to an auxiliary set of filtering molecules. More specifically, the system can determine, for each input molecule, whether the input molecule satisfies a matching criterion with each filtering molecule in the set of filtering molecules. The system can then determine whether to filter the input molecule based at least in part on whether the input molecule satisfies the matching criterion with each filtering molecule in the set of filtering molecules. Examples techniques for filtering a set of input molecules using an auxiliary set of filtering molecules is described in detail with reference to step 208 of FIG. 2.

Each chemical computation node can include any appropriate number of transformation operations. For instance, a chemical computation node can include a sequence of 1, 5, or 10 transformation operations.

The system can receive the data specifying the chemical computation graph from a user, e.g., by way of a user interface, e.g., a text-based or graphical user interface.

The data specifying the chemical computation graph can specify the topology of the chemical computation graph, e.g., by identifying how many chemical computation nodes are included in the chemical computation graph, and which chemical computation nodes are connected by edges.

The data specifying the chemical computation graph can further define, for each chemical computation node, a respective sequence of one or more transformation operations to be implemented by the chemical computation node.

The data specifying the chemical computation graph can further designate one or more nodes in the chemical computation graph as input nodes and one or more nodes in the chemical computation graph as output nodes.

For instance, the user interface can be a graphical user interface that enables a user to visually construct a graph of chemical computation nodes, including by dragging and dropping elements representing nodes and edges in the chemical computation graph in an interactive window.

The system receives data that defines a respective set of input molecules to be provided to each chemical computation node in the chemical computation graph that has been designated as being an input node (504). The system can provide an interface that enables a user to specify a set of input molecules to be provided to an input node in the chemical computation graph in any of a variety of possible ways. For instance, the system can enable a user to specify input molecules to be provided to an input node by inputting text-based representations of the molecules (e.g., as SMILES strings) or visual representations of the molecules (e.g., by graphically drawing the molecules by way of a graphical user interface). As another example, the system can enable a user to specify input molecules to be provided to an input node by selecting an existing library of molecules, or by selecting a portion of an existing library of molecules, e.g., by selecting all the molecules in a library that satisfy certain criteria, e.g., based on properties of the molecules such as molecular weight, polar surface area, solubility, and so forth.

The system executes the chemical computation graph to generate, from each chemical computation node that is designated as an output node, a respective set of output molecules (506). Executing the chemical computation graph can refer to executing the operations of each chemical computation node in the chemical computation graph. For instance, the system can start by executing the operations of each chemical computation node that is designated as an input node, because the input sets of molecules to be processed by the input nodes are initially specified by the user. The system can then provide the sets of output molecules generated by the input nodes as inputs to other chemical computation nodes in the graph, i.e., in accordance with the routing configuration defined by the edges of the chemical computation graph. The system can thus incrementally execute each chemical computation node in the chemical computation graph, by executing each chemical computation node once the set of input nodes to the chemical computation node are available, e.g., as a result of being provided by a user or being generated as outputs of other chemical computation nodes.

In some implementations, the system executes the chemical computation graph using a collection of multiple computing units that execute operations of different chemical computation nodes in parallel. In particular, the system can execute a group of multiple chemical computation nodes in parallel if none of the chemical computation nodes in the group rely, either directly or indirectly, on the outputs generated by any of the other chemical computation nodes in the group. The system can execute the chemical computation graph by dynamically identifying chemical computation nodes that are eligible for execution (e.g., because all the input molecules for the chemical computation node are available) and assigning chemical computation nodes that are eligible for execution to respective computing units in the collection of multiple computing units. Executing the chemical computation graph in a parallelized and distributed manner, as described above, can reduce latency in generating the output of the chemical computation graph.

A computing unit may be, e.g., a computer, a core within a computer having multiple cores, or other hardware or software, e.g., a dedicated thread, within a computer capable of independently perform operations. The computing units may include processor cores, processors, microprocessors, special-purpose logic circuitry, e.g., an FPGA (field-programmable gate array) or an ASIC (application-specific integrated circuit), or any other appropriate computing units. In some examples, the computing units are all the same type of computing unit. In other examples, the computing units may be different types of computing units. For example, one computing unit may be a CPU while other computing units may be GPUs.

In some cases, as described above, the chemical computation graph includes one or more cyclical subgraphs, where each cyclical subgraph forms a respective cycle in the larger chemical computation graph. As part of executing the chemical computation graph, the system can iteratively execute each cyclical subgraph over a sequence of one or more iterations until a termination criterion from a set of termination criteria is satisfied.

In more detail, at each of iteration in a sequence of one or more iterations, the system can execute a cyclical subgraph by executing the operations of each node included in the cyclical subgraph. At each iteration before a final iteration, executing the cyclical subgraph includes generating one or more sets of output molecules that are processed by the cyclical subgraph at a next iteration in the sequence of iterations.

At each iteration of executing a cyclical subgraph, the system can evaluate each termination criterion in a set of termination criteria associated with the cyclical subgraph. In response to determining that one or more termination criteria have been satisfied, the system can determine that the current iteration is the final iteration of executing the cyclical subgraph. The system can then route the output molecules generated by the chemical computation nodes in the cyclic subgraph at the final execution iteration of the cyclic subgraph to other chemical computation nodes outside the cyclic subgraph as required.

Each cyclical subgraph can be associated with a respective set of one or more termination criteria. A few examples of possible termination criteria for execution of a cyclic subgraph of the chemical computation graph are described next.

In one example, the set of termination criteria can include a termination criterion that is satisfied when the cyclical sub-graph has been executed over a predefined number of iterations. The predefined number of iterations can be, e.g., 2, or 3, or 5 iterations.

As another example, the set of termination criteria include a termination criterion that is evaluated based on molecular scores associated with molecules generated by one or more chemical computation nodes in the cyclical sub-graph. For instance, at each iteration of executing a cyclical subgraph, the system can apply one or more filtering criteria to a set of molecules generated by the chemical computation nodes in the cyclical subgraph at the iteration. The system can determine that a termination criterion is satisfied based on the result of the filtering operation. For instance, the system can determine that a termination criterion is satisfied if at least a threshold number of molecules remain in the set of molecules produced by the cyclical subgraph at the iteration after the filtering operation has been applied. As another example, the system can determine that a termination criterion is satisfied if at least a threshold fraction of the set of molecules produced by the cyclical subgraph at the iteration remains after the filtering operation has been applied. Examples of filtering operations, including those based on molecular scores, are described in detail with reference to step 208 of FIG. 2.

The system provides a set of output molecules generated by the designated output nodes of the chemical computation graph as the output resulting from executing the chemical computing graph (508). The set of output molecules can include any appropriate number of molecules, e.g., 10, 100, or 1000 output molecules.

The system can output a representation of the set of output molecules, e.g., by providing a (visual or text-based) representation of the output molecules to a user by way of a user interface, or by storing data defining the output molecules in a memory, or by transmitting data defining the output molecules over a data communication network, e.g., the internet, e.g., for presentation by or storage in a different system.

In some cases, one or more output molecules generated by the chemical computation graph are selected for physical synthesis. The selected molecules can then be physically synthesized, experimentally tested, and in some cases, included in drugs that are administered to subjects to achieve a therapeutic effect, as described above with reference to FIG. 1.

Figure 6:
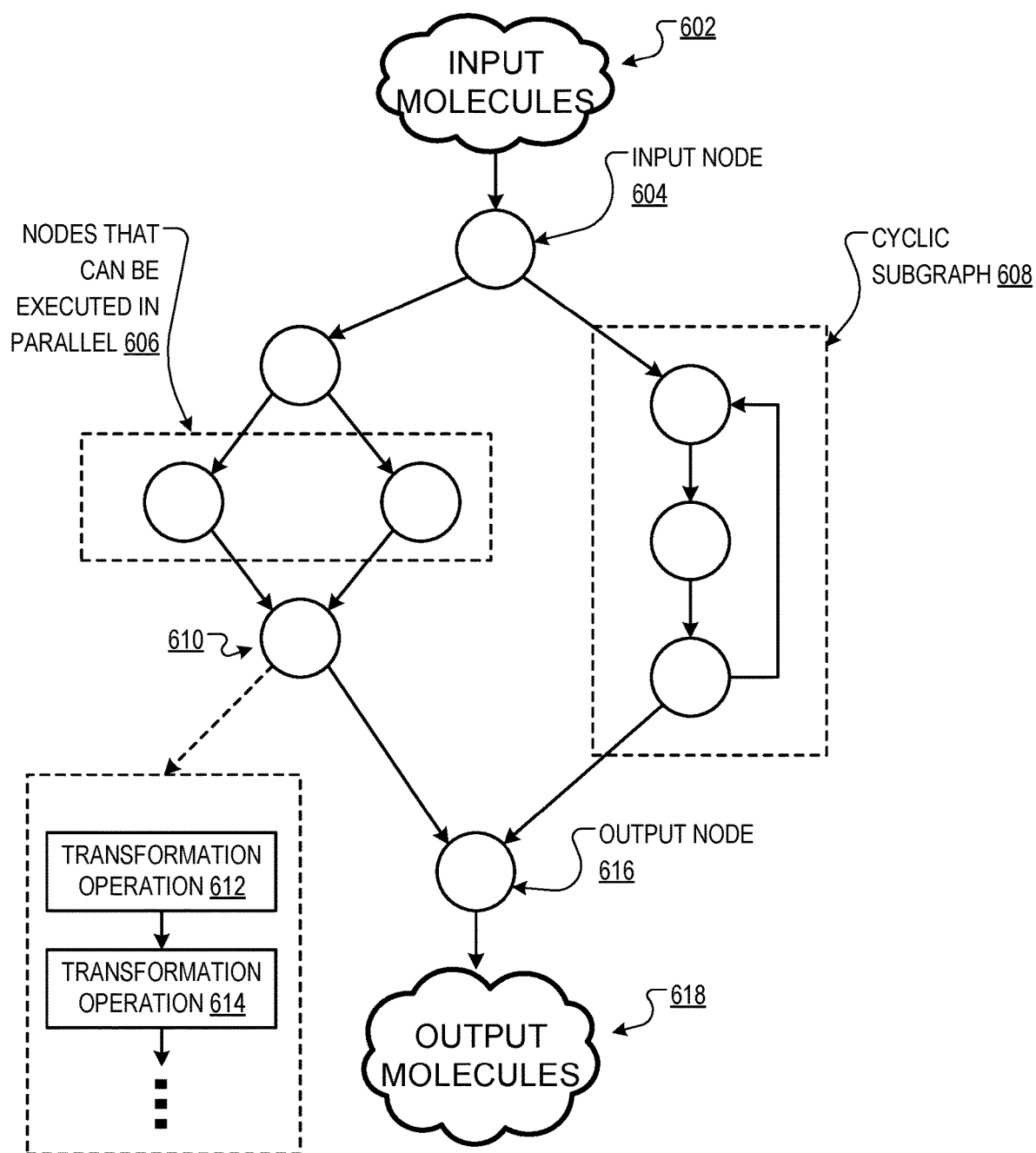
FIG. 6 provides an illustration of an example chemical computation graph.

FIG. 6 provides an illustration of an example chemical computation graph, where chemical computation nodes in the chemical computation graph are depicted as circles and edges in the chemical computation graph are depicted as arrows. The chemical computation graph receives a set of input molecules 602 at an input node 604, and upon execution of the chemical computation graph, generates a set of output molecules 618 by an output node 616 of the chemical computation graph. The chemical computation graph includes a cyclic subgraph 608 that defines a cycle in the larger chemical computation graph. The chemical computation graph includes chemical computation nodes that can be executed in parallel during execution of the chemical computation graph by a collection of multiple computing units, e.g., the nodes 606. Each chemical computation node can implement a respective sequence of one or more transformation operations, e.g., molecular generation or molecular filtering operations. For instance, the chemical computation node 610 implements the sequence of transformation operations 612, 614.

Figure 7:
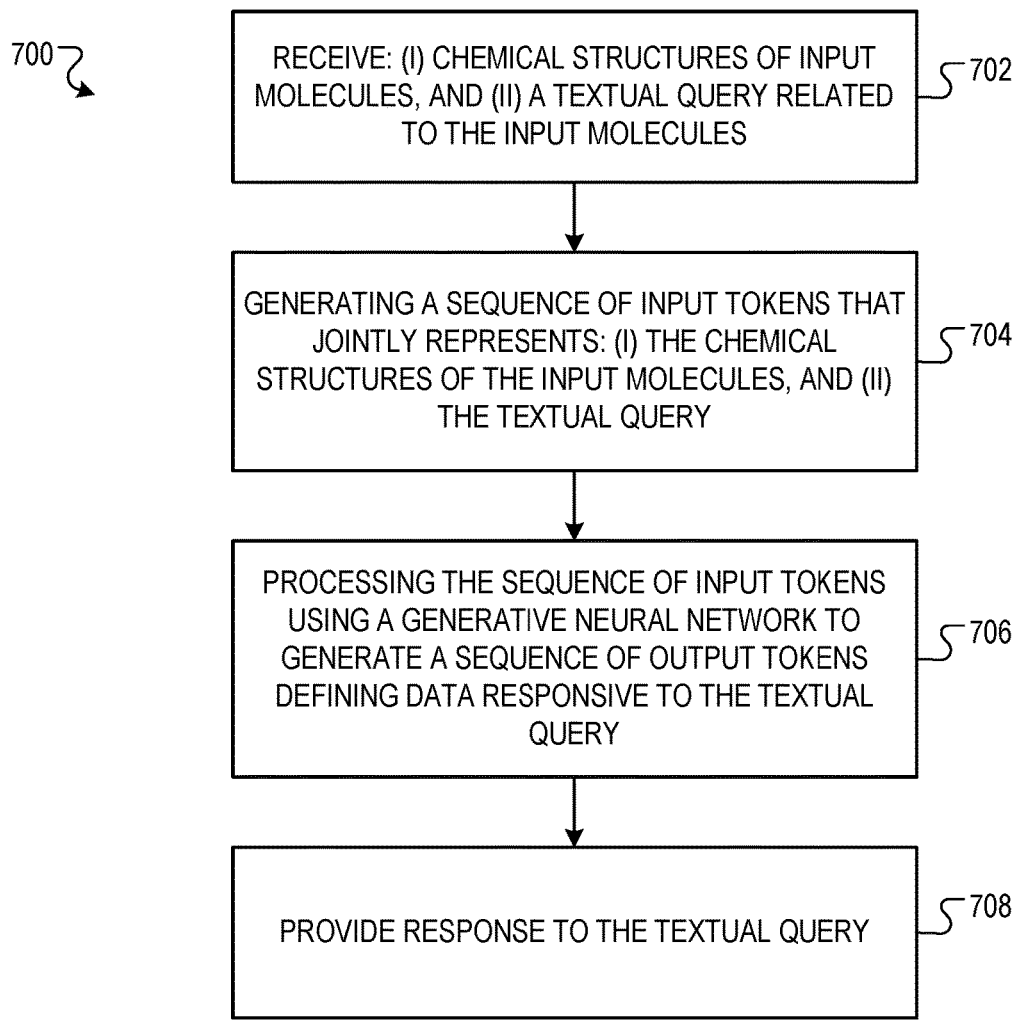
FIG. 7 is a flow diagram of an example process for generating a response to a textual query relating to one or more input molecules using a generative neural network.

FIG. 7 is a flow diagram of an example process 700 for generating a response to a textual query relating to one or more input molecules using a generative neural network. For convenience, the process 700 will be described as being performed by a system of one or more computers located in one or more locations. For example, a sequence computing system, e.g., the sequence computing system 112 of FIG. 1, appropriately programmed in accordance with this specification, can perform the process 700.

The system receives, from a user, data defining: (i) a chemical structure of each of one or more input molecules, and (ii) a textual query related to the one or more input molecules (702).

In more detail, for each input molecule, the system can receive data that defines the connectivity and types of atoms and bonds in the molecule, e.g., including data characterizing the branching structure of the molecule, any ring structures in the molecule, and the stereochemistry of the molecule (e.g., the geometry around double bonds and the configuration of chiral centers).

The system can enable the user to input data characterizing the chemical structure of an input molecule in any of a variety of possible ways. For instance, the system can provide a text-based interface that enables the user to input textual data, e.g., in the form of a SMILES string, that defines the structure of an input molecule. As another example, the system can provide an interactive visual interface that enables a user to construct two-dimensional (2D) or three-dimensional (3D) diagrams of molecules. As another example, the system can enable a user to select a molecule from a predefined library of molecules, each of which are already associated with a known chemical structure that is stored by the system. As another example the system can enable a user to specify: (i) a predefined library of molecules, and (ii) one or more molecular criteria, such that any molecule in the library is molecules that satisfies the molecular criteria is an input molecule. The molecular criteria can require that input molecules have a specified properties, e.g., in relation to molecular weight, polar surface area, solubility, toxicity, and so forth.

The system can enable the user to enter a free form textual query, e.g., by way of an interface that includes a text box where the user can input textual data specifying the textual query. The textual query can be any appropriate query relating to the input molecules. For instance, the textual query can include a request to generate output molecules, based on the one or more input molecules, that satisfy one or more molecular criteria. A few examples of molecular criteria for generating output molecules that can be specified by a textual query are described next.

In one example, a textual query can specify that an output molecule satisfies a molecular criterion if the output molecule results from attaching a pair of input molecules.

In another example, a textual query can designate one or more attachment points on each input molecule, and can specify that an output molecule satisfies a molecular criterion if the output molecule results from attaching a first input molecule and a second input molecule at the respective attachment points of the first input molecule and the second input molecule.

In another example, a textual query can identify: (i) one or more portions of each input molecule that are designated for replacement, and (ii) a set of one or more molecular fragments. In this example, the textual query can specify that an output molecule satisfies a molecular criterion if the output molecule results from replacing each portion of an input molecule that is designated for replacement by a respective molecular fragment from the set of molecular fragments.

In another example, the textual query can specify that an output molecule satisfies a molecular criterion if the output molecule is predicted to result from a chemical reaction involving an input molecule.

In another example, the textual query can specify that an output molecule satisfies a molecular criterion if the output molecules is an isostere of an input molecule.

In another example, the textual query can specify that an output molecule satisfies a molecular criterion if a similarity measure between the output molecule and an input molecule satisfies a threshold.

In another example, the textual query can specify that an output molecule satisfies a molecular criterion if a molecular score of the output molecule is within target range. The molecular score of the output molecule characterizes one or more of: a binding affinity of the output molecule for a binding target; a solubility of the output molecule; a toxicity of the output molecule; a binding affinity of the output molecule for one or more off-target binding sites; an absorption property of the output molecule; a distribution property of the output molecule; a metabolism property of the output molecule; an excretion property of the output molecule; a molecular weight property of the output molecule; or a topological polar surface area of the output molecule.

The examples described above provide illustrations of certain categories of textual queries that can be provided by users relating to generating output molecules, based on the one or more input molecules, that satisfy one or more molecular criteria. However, it will be appreciated that a textual query is not required to include any particular, predefined wording, or to define a request that falls neatly into a single one (or any) of the examples illustrated above. Rather, a user can provide a free form textual query, at any appropriate level of abstraction or granularity, that defines any appropriate request relating to the one or more input molecules.

The system generates a sequence of input tokens that jointly represents: (i) the chemical structure of each input molecule, and (ii) the textual query (704). For instance, the system can generate the sequence of input tokens by concatenating: (i) a sequence of tokens representing the chemical structure of each input molecule, and (ii) a sequence of tokens representing the textual query. The system can generate a sequence of tokens representing the chemical structure of an input molecule in any appropriate way, e.g., as a SMILES string or an InChI string. More generally, the sequence of input tokens can include interleaved subsequences of tokens representing chemical structures of input molecules and associated textual data, depending on the nature of the textual query and how the textual query is expressed. For instance, a query such as: "Can <molecule A> and <molecule B> react to form non-toxic, soluble products?" can be represented by interleaved strings of tokens representing text (e.g., "Can", "and", "react to form non-toxic, soluble products?") and molecules (e.g., <molecule A> and <molecule B>).

The system processes the sequence of input tokens using a generative neural network to generate a sequence of output tokens defining data responsive to the textual query (706). For instance, the sequence of output tokens can define a chemical structure of each of one or more output molecules, wherein the one or more output molecules are responsive to the textual query. As another example, the sequence of output tokens can define output textual data that is responsive to the textual query.

The generative neural network can have any appropriate neural network architecture that enables the generative neural network to perform its described functions. In particular, the generative neural network can include any appropriate types of neural network layers (e.g., fully connected layers, attention layers, recurrent layers, convolutional layers, message passing layers, and so forth) in any appropriate number (e.g., 5 layers, or 10 layers, or 100 layers) and connected in any appropriate configuration (e.g., as a directed graph of layers). In implementations where the generative neural network is an autoregressive neural network, e.g., as described with reference to FIG. 8, the generative neural network can have, e.g., an architecture that includes a sequence of self-attention neural network layers, e.g., a transformer decoder architecture.

An example process for processing a sequence of input tokens that defines a respective chemical structure of each of one or more input molecules and an associated textual query using a generative neural network to generate a sequence of output tokens defining data responsive to the textual query is described in detail with reference to FIG. 8. The sequence of output tokens can include represent textual data, or the chemical structures of one or more output molecules, or chemical computation operations that are executed as part of determining output molecules responsive to the textual query, as will be described in more detail below.

An example process for training an autoregressive generative neural network to process a sequence of input tokens that defines a respective chemical structure of each of one or more input molecules and an associated textual query to generate a sequence of output tokens defining data responsive to the textual query is described in detail with reference to FIG. 9.

The system outputs a response to the textual query (708). The response to the textual query is based on the sequence of output tokens generated by the generative neural network.

For instance, the sequence of output tokens generated by the generative neural network can include, for each of one or more output molecules, a respective sequence of tokens representing the output molecule (e.g., in the form of a SMILES string or an InChI string). Each sequence of tokens representing a respective output molecule can begin and end with a respective predefined delimiter token. The system can extract data defining each output molecule from the sequence of output tokens, and then provide data defining each of the output molecules. For example, the system can output a representation of the set of output molecules, e.g., by providing a (visual or text-based) representation of the output molecules to a user by way of a user interface, or by storing data defining the output molecules in a memory, or by transmitting data defining the output molecules over a data communication network, e.g., the internet, e.g., for presentation by or storage in a different system.

In another example, the sequence of output tokens generated by the generative neural network represents can include textual data (e.g., in addition or as an alternative to representing one or more output molecules, as described above). The system can extract the textual data from the sequence of output tokens and provide the textual data to the user, e.g., by presenting the textual data on a display by way of a user interface.

In some cases, the sequence of output tokens defines a set of output molecules, and one or more of the output molecules are selected for physical synthesis. The selected molecules can then be physically synthesized, experimentally tested, and in some cases, included in drugs that are administered to subjects to achieve a therapeutic effect, as described above with reference to FIG. 1.

Figure 8:
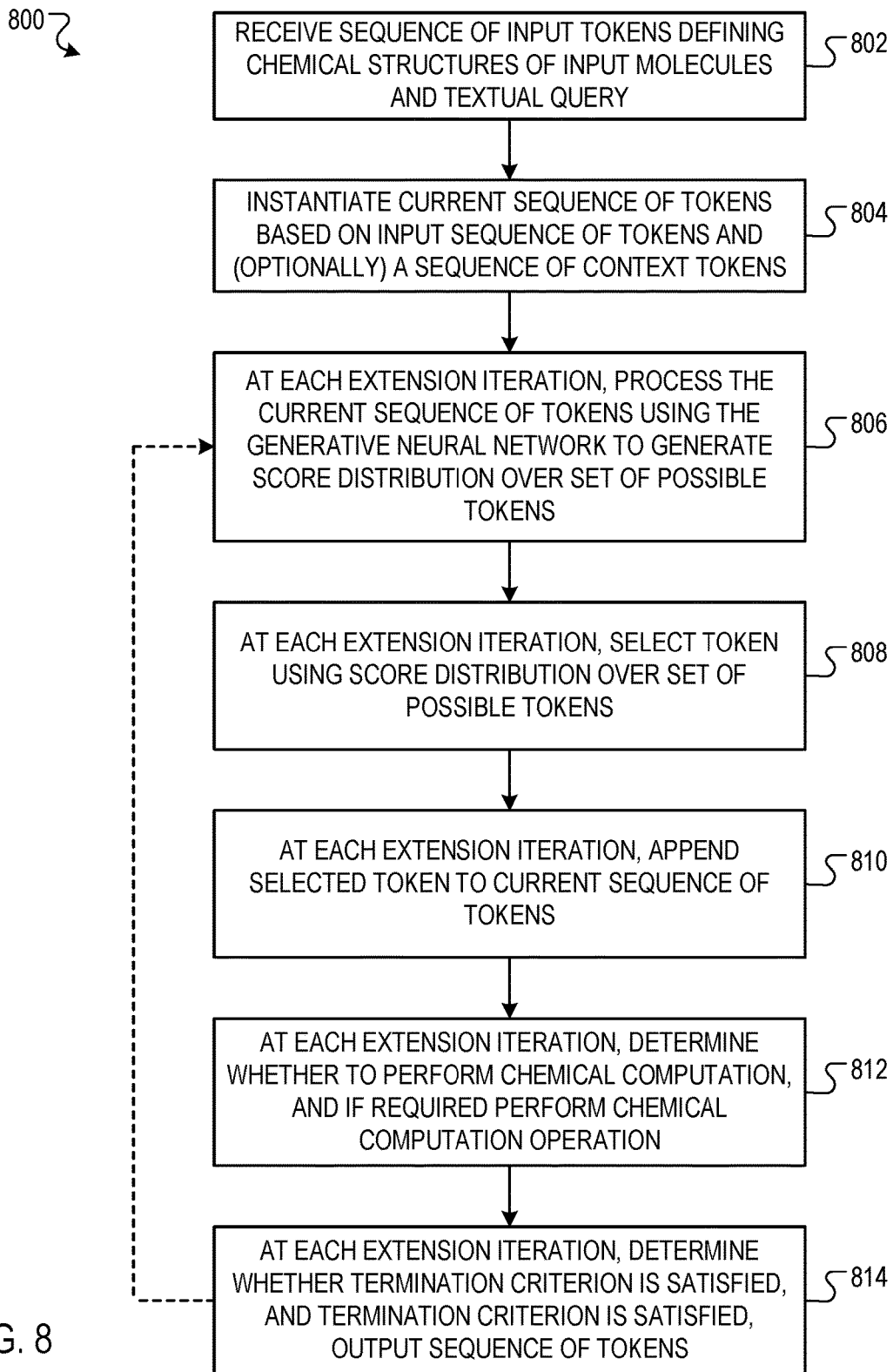
FIG. 8 is a flow diagram of an example process for processing a sequence of input tokens that defines a respective chemical structure of each of one or more input molecules and an associated textual query using a generative neural network to generate a sequence of output tokens defining data responsive to the textual query.

FIG. 8 is a flow diagram of an example process 800 for processing a sequence of input tokens that defines a respective chemical structure of each of one or more input molecules and an associated textual query using a generative neural network to generate a sequence of output tokens defining data responsive to the textual query. For convenience, the process 800 will be described as being performed by a system of one or more computers located in one or more locations. For example, a sequence computing system, e.g., the sequence computing system 112 of FIG. 1, appropriately programmed in accordance with this specification, can perform the process 800.

The system receives the sequence of input tokens that defines the respective chemical structure of each of one or more input molecules and the associated textual query (802).

The system instantiates a current sequence of tokens (804).

In some cases, the system defines the current sequence of tokens as the sequence of input tokens, i.e., as received at step 802.

In some cases, the system generates the current sequence of tokens by concatenating: (i) the sequence of input tokens, and (ii) a sequence of context tokens. The sequence of context tokens can represent a set of contextual information that may be relevant to responding to the textual query. For instance, the sequence of context tokens may define, for each molecule in a predefined library of molecules, a chemical structure of the molecule and one or more properties of the molecule. As another example, the sequence of context tokens can define a library of chemical reaction tuples, where each chemical reaction tuple specifies: a set of reactant molecules; a chemical reaction; and a set of product molecules resulting from the set of reactant molecules undergoing the chemical reaction.

The system autoregressively extends the current sequence of tokens (starting from the initial sequence of tokens determined at step 804) using the generative neural network until a termination criterion is satisfied.

More specifically, at each extension iteration in a sequence of extension iterations, the system processes a network input that includes the current sequence of tokens, using the generative neural network and in accordance with values of a set of generative neural network parameters, to generate a score distribution over a set of tokens (806).

The set of tokens can include any tokens representing any appropriate type of data. A few examples of types of tokens that can be included in the set of tokens are described next.

In one example, the set of tokens can include tokens representing, e.g., atoms, bonds, branches, ring structures, and so forth. The set of tokens can thus include tokens that allow the current sequence of tokens to express and define output molecules.

In another example, the set of tokens can include tokens representing textual data, e.g., textual characters, numbers, punctuation, and so forth. The set of tokens can thus include tokens that allow the current sequence of tokens to express and define output text.

In another example, the set of tokens can include tokens that enable the current sequence of tokens to specify respective chemical computation operations. A few examples of possible chemical computation operations are described next.

In one example, a chemical computation operation can be a molecule generation operation, i.e., an operation that is parametrized by a set of molecular generation criteria and that operates on a set of input molecules to generate a set of output molecules, where each output molecule satisfies the set of molecular generation criteria.

Examples of molecular generation criteria include: attachment criteria, chemical reaction criteria, and scaffolding criteria. Attachment criteria specify that output molecules should be generated by attaching two or more molecules from one or more input sets of molecules, or by replacing one or more portions of a molecule by respective molecular fragments from a set of molecular fragments. Chemical reaction criteria specify that output molecules are generated by chemically reacting one or more molecules from a set of input molecules in accordance with one or more chemical reactions from a set of chemical reactions. Scaffolding criteria specify that output molecules should be generated as completions of a scaffold molecule, where the scaffold molecule is represented by a sequence of tokens including one or more masked tokens representing unspecified parts of the scaffold molecule.

Attachment criteria, chemical reaction criteria, and scaffolding criteria are described in detail with reference to step 202 of FIG. 2.

In another example, a chemical computation operation can be a molecule filtering operation, i.e., an operation that is parameterized by a set of filtering criteria and that operates on a set of input molecules to filter (remove) any molecules from the set of input molecules that satisfy one or more of the filtering criteria.

In some cases, to implement a molecule filtering operation, the system generates, for each input molecule in a set of input molecules, one or more respective molecular scores that each characterize a respective property of the input molecule. Generating molecular scores for candidate molecules is described in detail with reference to step 206 of FIG. 2. The system can then filter the set of input molecules using filtering criteria that are based on the molecular scores for the input molecules. Example techniques for filtering a set of molecules based on molecular scores associated with molecules in the set of molecules is described in detail with reference to step 208 of FIG. 2.

In some cases, the system can implement a filtering operation with reference to an auxiliary set of filtering molecules. More specifically, the system can determine, for each input molecule, whether the input molecule satisfies a matching criterion with each filtering molecule in the set of filtering molecules. The system can then determine whether to filter the input molecule based at least in part on whether the input molecule satisfies the matching criterion with each filtering molecule in the set of filtering molecules. Examples techniques for filtering a set of input molecules using an auxiliary set of filtering molecules is described in detail with reference to step 208 of FIG. 2.

In another example, a chemical computation operation can be an operation that involves executing a chemical computation graph that includes a set of chemical computation nodes and a set of edges. Each chemical computation node is configured to receive a first set of molecules, and to process the first set of molecules, in accordance with a sequence of one or more transformation operations associated with the chemical computation node, to generate a second set of molecules. Each edge connects a respective first chemical computation node to a respective second chemical computation node and defines that a set of molecules generated by the first chemical computation node should be provided as an input to a second chemical computation node.

The set of tokens can include any appropriate tokens that enable the current sequence of tokens to specify respective chemical computation operations.

For instance, the current sequence of tokens can include binary tokens that enable specification of a binary adjacency matrix for a chemical computation graph.

As another example, the set of tokens can include tokens identifying respective chemical reactions from a set of chemical reactions, e.g., to enable specification of molecule generation operations involving chemical reaction criteria.

As another example, the set of tokens can include masked tokens, e.g., to enable specification of molecule generation operations involving generating completions of scaffold molecules.

As another example, the set of tokens can include tokens representing respective types of molecular scores (e.g., characterizing molecule properties such as toxicity, solubility, binding affinity, and so forth), e.g., to enable specification of molecule filtering operations based on molecular scores.

As another example, the set of tokens can include various delimiter tokens.

For instance, the set of tokens can include a delimiter token indicating that the start of a sequence of tokens representing a chemical computation operation.

As another example, the set of tokens can include a delimiter token indicating the end of a sequence of tokens representing a chemical computation operation.

As another example, the set of tokens can include delimiter tokens representing the start or end of a sequence of tokens representing data specifying respective molecules to be operated on by a chemical computation operation.

As another example, the set of tokens can include delimiter tokens representing the start or end of a sequence of tokens representing respective parameters of a chemical computation operation, e.g., the start or end of a sequence of tokens specifying an adjacency matrix of a chemical computation graph.

As another example, the set of tokens can include a delimiter token representing that tokens following the delimiter token represent data to be output to a user as a response to the textual query included in the sequence of input tokens, e.g., as described with reference to step 708 of FIG. 7.

As another example, the set of tokens can include an end-of-sequence (EOS) token representing that the final token in a sequence of tokens generated by the generative neural network.

At each extension iteration, the system then selects a token from the set of tokens in accordance with the score distribution over the set of tokens (808). For instance, the system can randomly sample a token from the set of tokens in accordance with the score distribution over the set of tokens, e.g., from a probability distribution that is generated by processing the score distribution over the set of tokens using a soft-max function.

At each extension iteration, the system appends the selected token to the current sequence of tokens (810).

At each extension iteration, the system determines whether to perform a chemical computation operation (812). In particular, the system evaluates whether a suffix of the current sequence of tokens defines a chemical computation operation. (A "suffix" of the current sequence of tokens refers to a contiguous group of tokens that extends to the end of the current sequence of tokens). For instance, the system can determine that a suffix of the current sequence of tokens defines a chemical computation operation if a suffix of the current sequence of tokens includes: (i) a first token delimiting the start of the definition of a chemical computation operation, and (ii) a last token delimiting the end of the definition of the chemical computation operation.

In response to determining that a chemical computation operation should be performed, the system extracts the suffix of the current sequence of tokens that defines the chemical computation operation, and then performs the specified chemical computation operation. The chemical computation operation can be, e.g., a molecular generation operation, or a molecular filtering operation, or an operation involving execution of a chemical computation graph, as described above.

The system can obtain a set of one or more output molecules generated as a result of the chemical computation operation, represent the set of one or more output molecules as a sequence of tokens, and then concatenate the sequence of tokens representing the set of one or more output molecules to the current sequence of tokens.

The system evaluates whether a termination criterion is satisfied (814). The termination criterion can be, e.g., that the selected token is a predefined "end-of-sequence" (EOS) token, or that a predefined maximum number of extension iterations have been performed. In response to determining that the termination criterion is not satisfied, the system can proceed to the next extension iteration. In response to determining that the termination criterion is satisfied, the system can terminate the process of extending the current sequence of tokens and designate the current sequence of tokens as the sequence of output tokens.

Figure 9:
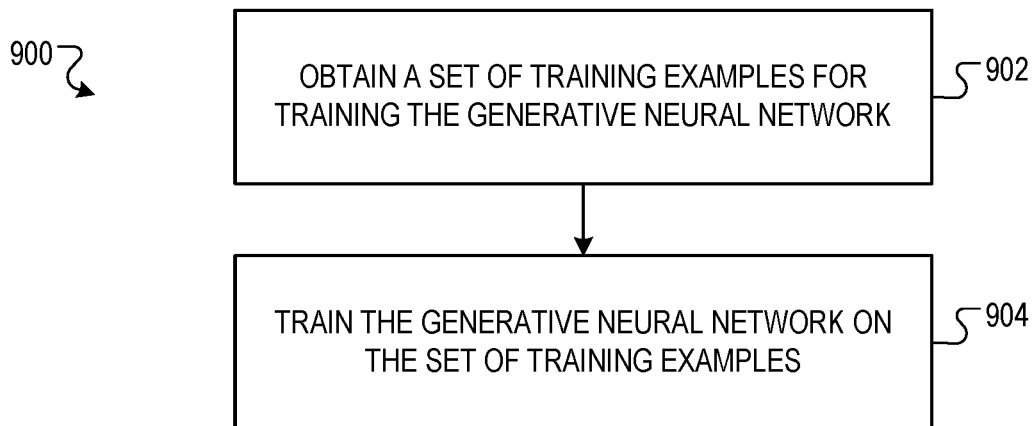
FIG. 9 is a flow diagram of an example process for training a generative neural network to process a sequence of input tokens that defines a respective chemical structure of each of one or more input molecules and an associated textual query to generate a sequence of output tokens defining data responsive to the textual query.

FIG. 9 is a flow diagram of an example process 900 for training a generative neural network to process a sequence of input tokens that defines a respective chemical structure of each of one or more input molecules and an associated textual query to generate a sequence of output tokens defining data responsive to the textual query. For convenience, the process 900 will be described as being performed by a system of one or more computers located in one or more locations. For example, a sequence computing system, e.g., the sequence computing system 112 of FIG. 1, appropriately programmed in accordance with this specification, can perform the process 900.

The system obtains a set of training examples for training the generative neural network (902). Each training example includes a respective sequence of tokens.

For one or more of the training examples, the sequence of tokens can represent natural language text.

For one or more of the training examples, the sequence of tokens can represent both natural language text and chemical structure data that defines a respective chemical structure of each of one or more input molecules.

For one or more of the training examples, the sequence of tokens includes: (i) a prefix that represents chemical structure data for one or more input molecules and natural language text that represents a query related to the one or more input molecules, and (ii) a suffix that represents data responsive to the query from the suffix.

For one or more of the training examples, the sequence of tokens includes a suffix that (as described above) represents data responsive to the query in the suffix and, in particular, includes data specifying one or more chemical computation operations. The chemical computation operations that include molecular generation operations, molecular filtering operations, operations that involve executing a chemical computation graph, or any combination thereof.

The system trains the generative neural network on the set of training examples (904).

In some implementations, the system pre-trains the generative neural network on a first set of training examples, wherein one or more of the training examples in the first set of training examples each include a respective sequence of tokens representing natural language text. The system then fine-tunes the generative neural network on a second set of training examples, wherein one or more of the training examples in the second set of training examples each include a respective sequence of tokens representing natural language text and chemical structure data.

The system can train the generative neural network on the set of training examples in any appropriate way. For instance, the system can train the generative neural network to perform a next token prediction task. More specifically, for each training example and for each of one or more prefixes of the sequence of tokens of the training example, the system can process the prefix of the sequence of tokens to generate a score distribution over a set of tokens. The system can evaluate an objective function that measures, for each prefix of the sequence of tokens, an error (e.g., a cross-entropy error) between: (i) the token following the prefix in the sequence of tokens, and (ii) the score distribution over the set of tokens that is generated by the generative neural network by processing the prefix of the sequence of tokens. The system can determine gradients of the objective function with respect to the parameters in a set of parameters of the generative neural network, e.g., using backpropagation. The system can then adjust the current values of the set of parameters of the generative neural network using the gradients, e.g., in accordance with the update rule of an appropriate gradient descent optimization algorithm, e.g., RMSprop or Adam.

Figure 10:
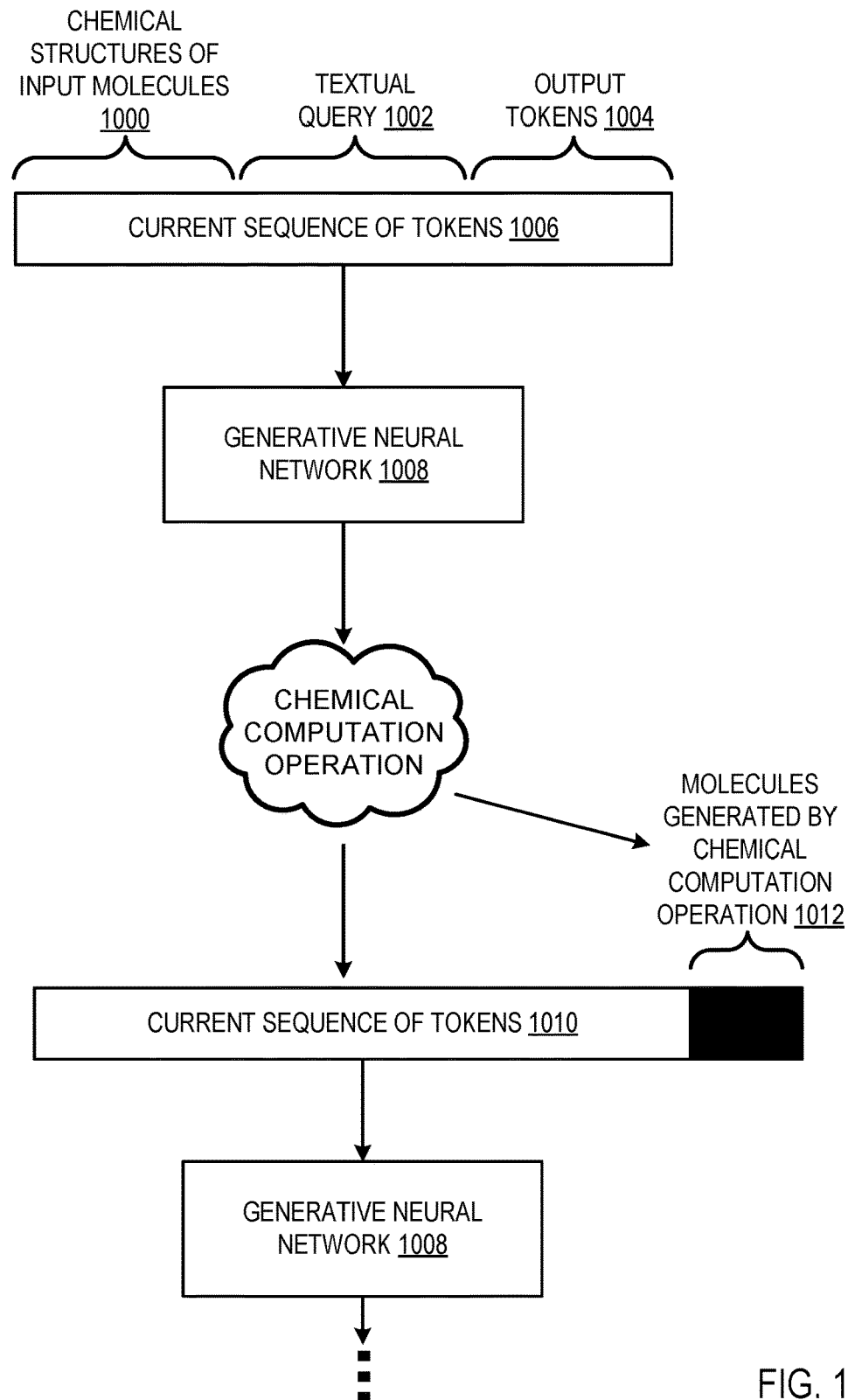
FIG. 10 is an illustration of example operations that can be performed by an autoregressive generative neural network as part of generating a sequence of output tokens responsive to a textual query related to one or more input molecules.

FIG. 10 is an illustration of example operations that can be performed by an autoregressive generative neural network as part of generating a sequence of output tokens responsive to a textual query related to one or more input molecules. As described with reference to FIG. 8, the system can initialize a current sequence of tokens 1006 that includes: (i) tokens representing the chemical structure of the input molecules 1000, and (ii) tokens representing the textual query 1002. The system can use the generative neural network to iteratively extend the current sequence of tokens over a sequence of extension iterations. In particular, at each extension iteration, the generative neural network can process the current sequence of tokens to generate a score distribution over a set of possible tokens, select a token from the set of possible tokens, and then append the token to the current sequence of tokens. (The output tokens 1004 in FIG. 10 illustrate tokens appended to the initial sequence of tokens using the generative neural network 1008).

In some cases, the system can determine that a suffix of the current sequence of tokens specifies a chemical computation operation 1008, e.g., a molecular generation operation, or a molecular filtering operation, or an operation involving execution of a chemical computation graph. The system can then perform the chemical computation operation to generate a resulting set of output molecules, and append new tokens representing the output molecules 1012 to the current sequence of tokens 1010. The system can then provide the current sequence of tokens 1010 for processing by the generative neural network 1008 at a next extension iteration, and proceed with iteratively extending the current sequence of tokens until a termination criterion is satisfied.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, or a Jax framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by one or more computers, the method comprising:
presenting an interactive graphical user interface to a user on a display of a user device;
receiving, from the user and by way of the interactive graphical user interface, user input data defining: (i) a chemical structure of each of one or more input molecules, and (ii) a natural language textual query related to the one or more input molecules;
generating a sequence of input tokens that jointly represents: (i) the chemical structure of each input molecule, and (ii) the natural language textual query; and
processing the sequence of input tokens that jointly represents: (i) the chemical structure of each input molecule, and (ii) the natural language textual query, using a generative neural network to generate a sequence of output tokens defining data responsive to the natural language textual query, comprising:
sequentially generating each output token in the sequence of output tokens starting from a first output token in the sequence of output tokens;
wherein for one or more positions in the sequence of output tokens, generating the output token at the position comprises:
processing a network input that comprises: (a) the sequence of input tokens that jointly represents the chemical structure of each input molecule and the natural language textual query, and (b) a respective output token at each of one or more preceding positions in the sequence of output tokens, using the generative neural network, to generate a score distribution over a set of tokens; and selecting the output token for the position in accordance with the score distribution; and after generating the sequence of output tokens by, for each of one or more positions in the sequence of output tokens, selecting the output token for the position in accordance with the score distribution generated by the generative neural network:

presenting, to the user and by way of the interactive graphical user interface, a representation of the sequence of output tokens defining data responsive to the natural language textual query from the user, wherein the representation of the sequence of output tokens comprises: (i) a sequence of output text, (ii) a respective visual rendering of a chemical structure of each of one or more output molecules, or (iii) both.

2. The method of claim 1, wherein the generative neural network is an autoregressive neural network.

3. The method of claim 1, wherein for one or more positions in the sequence of output tokens, the network input to the generative neural network further comprises the sequence of input tokens.

4. The method of claim 1, wherein for one or more positions in the sequence of output tokens, the network input to the generative neural network further comprises a predefined sequence of context tokens representing at least chemical structure data.

5. The method of claim 1, wherein for one or more positions in the sequence of output tokens, selecting the output token for the position in accordance with the score distribution comprises:

randomly sampling a token from the set of tokens in accordance with the score distribution over the set of tokens.

6. The method of claim 1, further comprising, for one or more positions in the sequence of output tokens, after selecting the output token for the position:

determining that a suffix of the sequence of output tokens defines a chemical computation operation;

in response, executing the chemical computation operation to generate data defining a set of molecules; and appending tokens representing the set of molecules generated by the chemical computation operation to the sequence of output tokens.

7. The method of claim 6, wherein executing the chemical computation operation comprises performing a molecule generation operation, wherein the molecule generation operation is parameterized by a set of molecular generation criteria and operates on a set of input molecules to generate a set of output molecules, wherein each output molecule satisfies the set of molecular generation criteria.

8. The method of claim 7, wherein the set of molecular generation criteria comprise an attachment criteria specifying that: (i) each output molecule should be generated by attaching two or more input molecules, or (ii) each output molecule should be generated by replacing one or more portions of an input molecule with a respective molecular fragment from a set of molecular fragments.

9. The method of claim 7, wherein the set of molecular generation criteria comprise chemical reaction criteria specifying that output molecules are generated by chemically reacting one or more input molecules in accordance with one or more chemical reactions.

10. The method of claim 6, wherein executing chemical computation operation comprises performing a molecule filtering operation, wherein the molecule filtering operation is parametrized by a set of filtering criteria and operates on a set of input molecules to remove any molecules from the set of input molecules that satisfy one or more filtering criteria in the set of filtering criteria.

11. The method of claim 10, wherein the set of filtering criteria are based on molecular scores of input molecules, wherein a molecular score for an input molecule characterizes a property of the input molecule.

12. The method of claim 1, wherein the sequence of output tokens defines a chemical structure of each of one or more output molecules, wherein the one or more output molecules are responsive to the textual query.

13. The method of claim 1, wherein the sequence of output tokens defines a chemical computation graph, wherein executing the chemical computation graph causes generation of one or more output molecules that are responsive to the textual query.

14. The method of claim 13, wherein the chemical computation graph comprises a set of chemical computation nodes and a set of edges;

each chemical computation node is configured to perform operations comprising:

receiving a first set of molecules; and processing the first set of molecules, in accordance with a sequence of one or more transformation operations associated with the chemical computation node, to generate a second set of molecules; and each edge connects a respective first chemical computation node to a respective second chemical computation node and defines that a set of molecules generated by the first chemical computation node should be provided as an input to a second chemical computation node.

15. The method of claim 13, further comprising executing the chemical computation graph to generate one or more output molecules that are responsive to the textual query.

16. The method of claim 1, wherein generating the sequence of input tokens that jointly represents: (i) the chemical structure of each input molecule, and (ii) the textual query, comprises:

concatenating: (i) a sequence of tokens representing the chemical structure of each input molecule, and (ii) a sequence of tokens representing the textual query.

17. A system comprising:

one or more computers; and one or more storage devices communicatively coupled to the one or more computers, wherein the one or more storage devices store instructions that, when executed by the one or more computers, cause the one or more computers to perform operations comprising:

presenting an interactive graphical user interface to a user on a display of a user device;

receiving, from the user and by way of the interactive graphical user interface, user input data defining: (i) a chemical structure of each of one or more input molecules, and (ii) a natural language textual query related to the one or more input molecules;

generating a sequence of input tokens that jointly represents: (i) the chemical structure of each input molecule, and (ii) the natural language textual query; and processing the sequence of input tokens that jointly represents: (i) the chemical structure of each input molecule, and (ii) the natural language textual query, using a generative neural network to generate a sequence of output tokens defining data responsive to the natural language textual query, comprising:

sequentially generating each output token in the sequence of output tokens starting from a first output token in the sequence of output tokens;

wherein for one or more positions in the sequence of output tokens, generating the output token at the position comprises:

processing a network input that comprises: (a) the sequence of input tokens that jointly represents the chemical structure of each input molecule and the natural language textual query, and (b) a respective output token at each of one or more preceding positions in the sequence of output tokens, using the generative neural network, to generate a score distribution over a set of tokens; and selecting the output token for the position in accordance with the score distribution; and after generating the sequence of output tokens by, for each of one or more positions in the sequence of output tokens, selecting the output token for the position in accordance with the score distribution generated by the generative neural network:

presenting, to the user and by way of the interactive graphical user interface, a representation of the sequence of output tokens defining data responsive to the natural language textual query from the user, wherein the representation of the sequence of output tokens comprises: (i) a sequence of output text, (ii) a respective visual rendering of a chemical structure of each of one or more output molecules, or (iii) both.

18. One or more non-transitory computer storage media storing instructions that when executed by one or more computers cause the one or more computers to perform operations comprising:

presenting an interactive graphical user interface to a user on a display of a user device;

receiving, from the user and by way of the interactive graphical user interface, user input data defining: (i) a chemical structure of each of one or more input molecules, and (ii) a natural language textual query related to the one or more input molecules;

generating a sequence of input tokens that jointly represents: (i) the chemical structure of each input molecule, and (ii) the natural language textual query; and processing the sequence of input tokens that jointly represents: (i) the chemical structure of each input molecule, and (ii) the natural language textual query, using a generative neural network to generate a sequence of output tokens defining data responsive to the natural language textual query, comprising:

sequentially generating each output token in the sequence of output tokens starting from a first output token in the sequence of output tokens;

wherein for one or more positions in the sequence of output tokens, generating the output token at the position comprises:

processing a network input that comprises: (a) the sequence of input tokens that jointly represents the chemical structure of each input molecule and the natural language textual query, and (b) a respective output token at each of one or more preceding positions in the sequence of output tokens, using the generative neural network, to generate a score distribution over a set of tokens; and selecting the output token for the position in accordance with the score distribution; and after generating the sequence of output tokens by, for each of one or more positions in the sequence of output tokens, selecting the output token for the position in accordance with the score distribution generated by the generative neural network:

presenting, to the user and by way of the interactive graphical user interface, a representation of the sequence of output tokens defining data responsive to the natural language textual query from the user, wherein the representation of the sequence of output tokens comprises: (i) a sequence of output text, (ii) a respective visual rendering of a chemical structure of each of one or more output molecules, or (iii) both.

19. The non-transitory computer storage media of claim 18, wherein the operations further comprise, for one or more positions in the sequence of output tokens, after selecting the output token for the position:

determining that a suffix of the sequence of output tokens defines a chemical computation operation;

in response, executing the chemical computation operation to generate data defining a set of molecules; and appending tokens representing the set of molecules generated by the chemical computation operation to the sequence of output tokens.

20. The non-transitory computer storage media of claim 19, wherein executing the chemical computation operation comprises performing a molecule generation operation, wherein the molecule generation operation is parameterized by a set of molecular generation criteria and operates on a set of input molecules to generate a set of output molecules, wherein each output molecule satisfies the set of molecular generation criteria.

* * * * *

UNITED STATES PATENT AND TRADEMARK OFFICE
CERTIFICATE OF CORRECTION

PATENT NO. : 12,288,600 B2
APPLICATION NO. : 18/408042
DATED : April 29, 2025
INVENTOR(S) : Ben Sklaroff et al.

Page 1 of 1

It is certified that error appears in the above-identified patent and that said Letters Patent is hereby corrected as shown below:

On the Title Page

Item (12), delete "Sklaroff" and insert --Sklaroff et al.--.

Item (72), in the inventor section, after "Ben Sklaroff, San Francisco, CA (US)", please insert the following:
--Kenneth Knute Leidal, Windham, NH (US)
Matteus Jiawei Pan, San Francisco, CA (US)
Korrawat Pruegsanusak, San Francisco, CA (US)
Zachary Joseph Kagin, San Francisco, CA (US)--.

Signed and Sealed this
Twenty-sixth Day of August, 2025

Coke Morgan Stewart
*Acting Director of the United States Patent and Trademark Office*